(12) United States Patent
Scherer et al.

(10) Patent No.: US 11,557,297 B2
(45) Date of Patent: Jan. 17, 2023

(54) SYSTEMS AND METHODS FOR ADAPTIVE HUMAN-MACHINE INTERACTION AND AUTOMATIC BEHAVIORAL ASSESSMENT

(71) Applicant: Embodied, Inc., Pasadena, CA (US)

(72) Inventors: Stefan Scherer, Santa Monica, CA (US); Aubrey Schick, Berkeley, CA (US); Nichole Marie Hurst, Los Angeles, CA (US); Sara Jenny Palencia, Los Angeles, CA (US); Josh Anon, Los Angeles, CA (US)

(*) Notice: Subject to any disclaimer, the term of this patent is extended or adjusted under 35 U.S.C. 154(b) by 691 days.

(21) Appl. No.: 16/675,640

(22) Filed: Nov. 6, 2019

(65) Prior Publication Data

US 2020/0152314 A1     May 14, 2020

Related U.S. Application Data

(60) Provisional application No. 62/758,361, filed on Nov. 9, 2018.

(51) Int. Cl.
*G10L 15/26* (2006.01)
*G06F 16/9032* (2019.01)
*G10L 15/22* (2006.01)

(52) U.S. Cl.
CPC ........ *G10L 15/26* (2013.01); *G06F 16/90332* (2019.01); *G10L 15/22* (2013.01)

(58) Field of Classification Search
None
See application file for complete search history.

(56) References Cited

U.S. PATENT DOCUMENTS

| | | | |
|---|---|---|---|
| 6,757,362 B1* | 6/2004 | Cooper | H04M 3/527 379/88.16 |
| 7,442,107 B1 | 10/2008 | Ueda | |
| 10,565,985 B1* | 2/2020 | Huang | G06F 3/167 |
| 11,024,304 B1* | 6/2021 | Smith | G10L 15/22 |
| 2002/0019193 A1 | 2/2002 | Maggiore | |
| 2002/0165642 A1 | 7/2002 | Sakaue et al. | |
| 2002/0169733 A1 | 11/2002 | Peters, II | |
| 2003/0182123 A1 | 9/2003 | Mitsuyoshi | |
| 2005/0033582 A1* | 2/2005 | Gadd | G10L 15/26 704/E15.04 |
| 2005/0149227 A1 | 7/2005 | Peters, II | |
| 2007/0128979 A1 | 6/2007 | Schackelford et al. | |
| 2010/0076750 A1 | 3/2010 | Cosatto et al. | |
| 2011/0004341 A1 | 1/2011 | Sarvadevabhatla | |
| 2011/0295392 A1 | 12/2011 | Cunnington | |
| 2012/0016678 A1* | 1/2012 | Gruber | G06N 5/041 704/E21.001 |
| 2012/0182392 A1 | 7/2012 | Kearns | |
| 2013/0078600 A1 | 3/2013 | Fischer | |

(Continued)

FOREIGN PATENT DOCUMENTS

| | | |
|---|---|---|
| CN | 111563140 A | 8/2020 |
| WO | WO/2019/144542 | 8/2019 |

OTHER PUBLICATIONS

European Extended Search Report, dated Apr. 11, 2022, Application No. 19846453.9-1002 / PCT/US2019045037, 21 pages.

(Continued)

*Primary Examiner* — Neeraj Sharma

(57) ABSTRACT

Systems and methods for human-machine interaction using a conversation system.

23 Claims, 14 Drawing Sheets

(56) References Cited

U.S. PATENT DOCUMENTS

| | | | |
|---|---|---|---|
| 2014/0244712 A1* | 8/2014 | Walters | G06Q 30/02 709/202 |
| 2014/0278413 A1* | 9/2014 | Pitschel | G10L 15/22 704/243 |
| 2014/0316570 A1 | 10/2014 | Sun | |
| 2014/0339589 A1 | 11/2014 | Uhrmann et al. | |
| 2015/0148953 A1 | 5/2015 | Laurent et al. | |
| 2016/0199977 A1 | 7/2016 | Breazeal | |
| 2017/0100842 A1 | 4/2017 | Le Borgne | |
| 2017/0113353 A1 | 4/2017 | Monceaux | |
| 2017/0125008 A1 | 5/2017 | Maisonnier et al. | |
| 2017/0160813 A1 | 6/2017 | Divakaran | |
| 2017/0206064 A1 | 7/2017 | Breazeal | |
| 2017/0311863 A1 | 11/2017 | Matsunaga | |
| 2017/0352351 A1 | 12/2017 | Kimura | |
| 2017/0358305 A1 | 12/2017 | Kudurshian et al. | |
| 2018/0068177 A1 | 3/2018 | Sakai | |
| 2018/0075659 A1 | 3/2018 | Browy | |
| 2018/0133900 A1 | 5/2018 | Breazeal et al. | |
| 2018/0229372 A1 | 8/2018 | Breazeal et al. | |
| 2018/0260680 A1 | 9/2018 | Finkelstein et al. | |
| 2018/0301151 A1 | 10/2018 | Mont-Reynaud et al. | |
| 2019/0008441 A1* | 1/2019 | Guzik | A61B 5/163 |
| 2019/0042988 A1 | 2/2019 | Brown et al. | |
| 2019/0248019 A1 | 8/2019 | Nelson | |
| 2019/0279639 A1 | 9/2019 | Ginsberg et al. | |
| 2019/0291277 A1 | 9/2019 | Oleynik | |
| 2019/0366538 A1 | 12/2019 | Laurent et al. | |
| 2020/0050173 A1 | 2/2020 | Scherer et al. | |
| 2020/0073938 A1* | 3/2020 | Losalka | G06F 40/35 |
| 2020/0074991 A1* | 3/2020 | Yalla | G06F 40/268 |
| 2020/0135041 A1* | 4/2020 | Arslan | G10L 15/26 |
| 2020/0218781 A1 | 7/2020 | Takano et al. | |
| 2021/0034959 A1 | 2/2021 | Wood | |
| 2021/0240927 A1* | 8/2021 | Zhao | G06F 40/279 |

OTHER PUBLICATIONS

International Search Report and Written Opinion of the International Search Authority, dated Oct. 29, 2019, PCT/US19/45037, 13 pages.

International Search Report and Written Opinion of the International Search Authority, dated Jun. 30, 2021, PCT/US21/20035, 12 pages.

International Search Report and Written Opinion of the International Search Authority, dated Aug. 9, 2021, PCT/US21/29297, 15 pages.

International Search Report and Written Opinion of the International Search Authority, dated May 18, 2021, PCT/US21/20056, 21 pages.

International Search Report and Written Opinion of the International Search Authority, dated Jun. 9, 2021, PCT/US21/20128, 10 pages.

International Search Report and Written Opinion of the International Search Authority, dated May 18, 2021, PCT/US21/20148, 12 pages.

International Search Report and Written Opinion of the International Search Authority, dated May 20, 2021, PCT/US21/20124, 8 pages.

International Search Report and Written Opinion of the International Search Authority, dated May 2, 2022, PCT/US22/14213, 21 pages.

* cited by examiner

```
Goal Definition Information 301

<Goal ID = 1 EvaluationModule = {emotion, smile}>
   {Goal definition}

<GoalLevel ID = 1 >
      {Goal Level definition}

<SupportLevel ID = 1>
         <Prompt ID = 1; Action = {prompt action 1} Frequency = 1>
      </SupportLevel>

<SupportLevel ID = 2>
         <Prompt ID = 1; Action = {prompt action 1} Frequency = 2>
         <Prompt ID = 2; Action = {prompt action 2} Frequency = 2>
      </SupportLevel>

<SupportLevel ID = 3>
         <Prompt ID = 1; Action = {prompt action 1} Frequency = 5>
         <Prompt ID = 2; Action = {prompt action 2} Frequency = 4>
      </SupportLevel>

</GoalLevel>

<GoalLevel ID = 2 >
      {Goal Level definition}

<SupportLevel ID = 1>
         <Prompt ID = 1; Action = {prompt action 1} Frequency = 1>
      </SupportLevel>

<SupportLevel ID = 2>
         <Prompt ID = 1; Action = {prompt action 1} Frequency = 2>
      </SupportLevel>

<SupportLevel ID = 3>
         <Prompt ID = 1; Action = {prompt action 1} Frequency = 5>
         <Prompt ID = 2; Action = {prompt action 3} Frequency = 5>
      </SupportLevel>

</GoalLevel>

</Goal>
```

FIGURE 3

SYSTEMS AND METHODS FOR ADAPTIVE HUMAN-MACHINE INTERACTION AND AUTOMATIC BEHAVIORAL ASSESSMENT

CROSS-REFERENCE TO RELATED APPLICATIONS

This application claims the benefit of U.S. Provisional Application Ser. No. 62/758,361, filed on 9 Nov. 2018, which is incorporated in its entirety by this reference.

TECHNICAL FIELD

This disclosure relates generally to human-machine interaction systems, and more specifically to new and useful systems and methods for adaptive human-machine interaction and automatic behavioral assessment.

BACKGROUND

Typical human-machine interaction systems receive user input received via an input device.

BRIEF DESCRIPTION OF THE FIGURES

FIG. 3 is a representation of an exemplary goal definition information, according to embodiments;

DESCRIPTION OF EMBODIMENTS

Figure 1A:
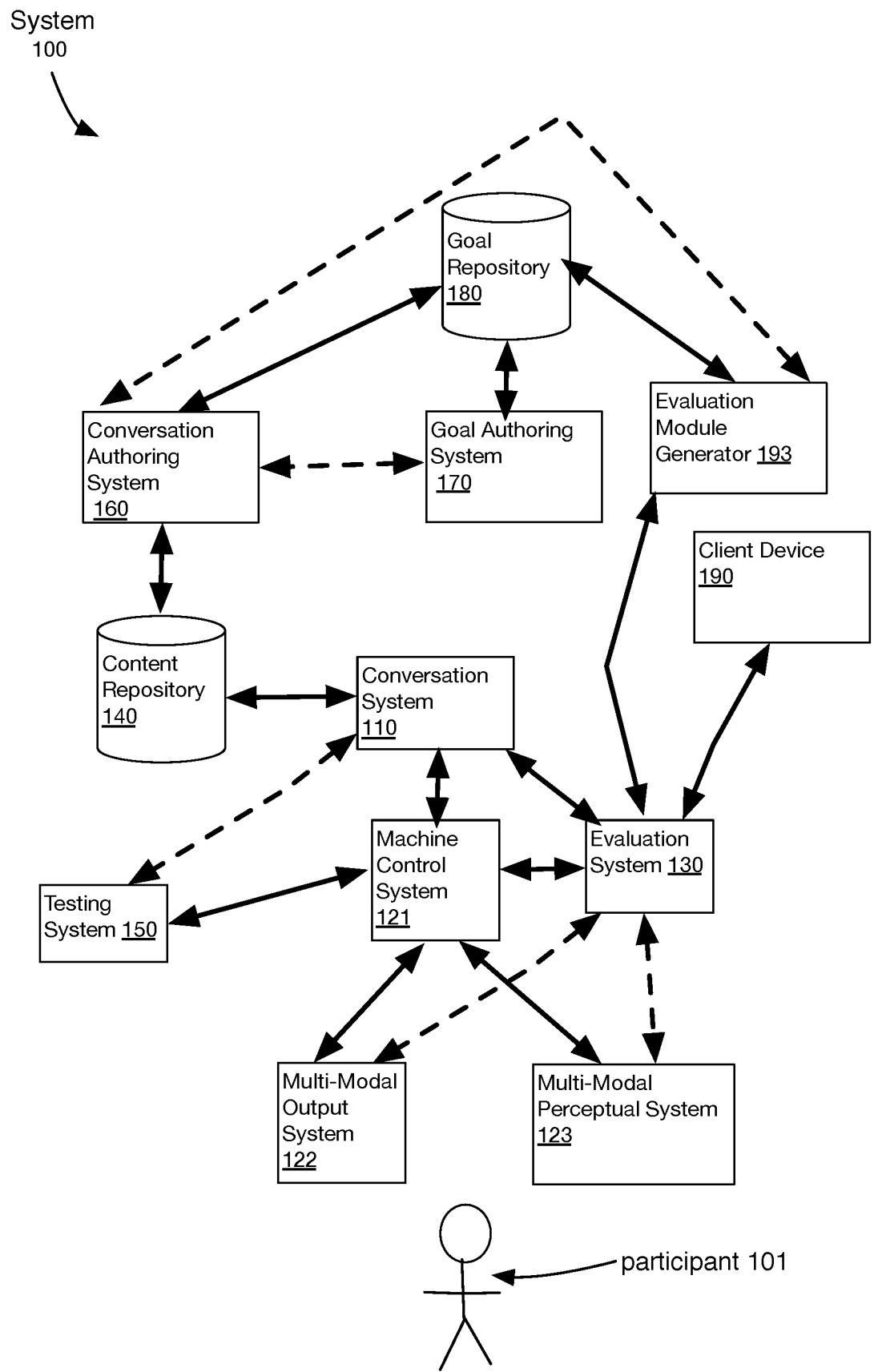
FIGS. 1A-F are schematic representations of systems, according to embodiments.
Figure 1B:
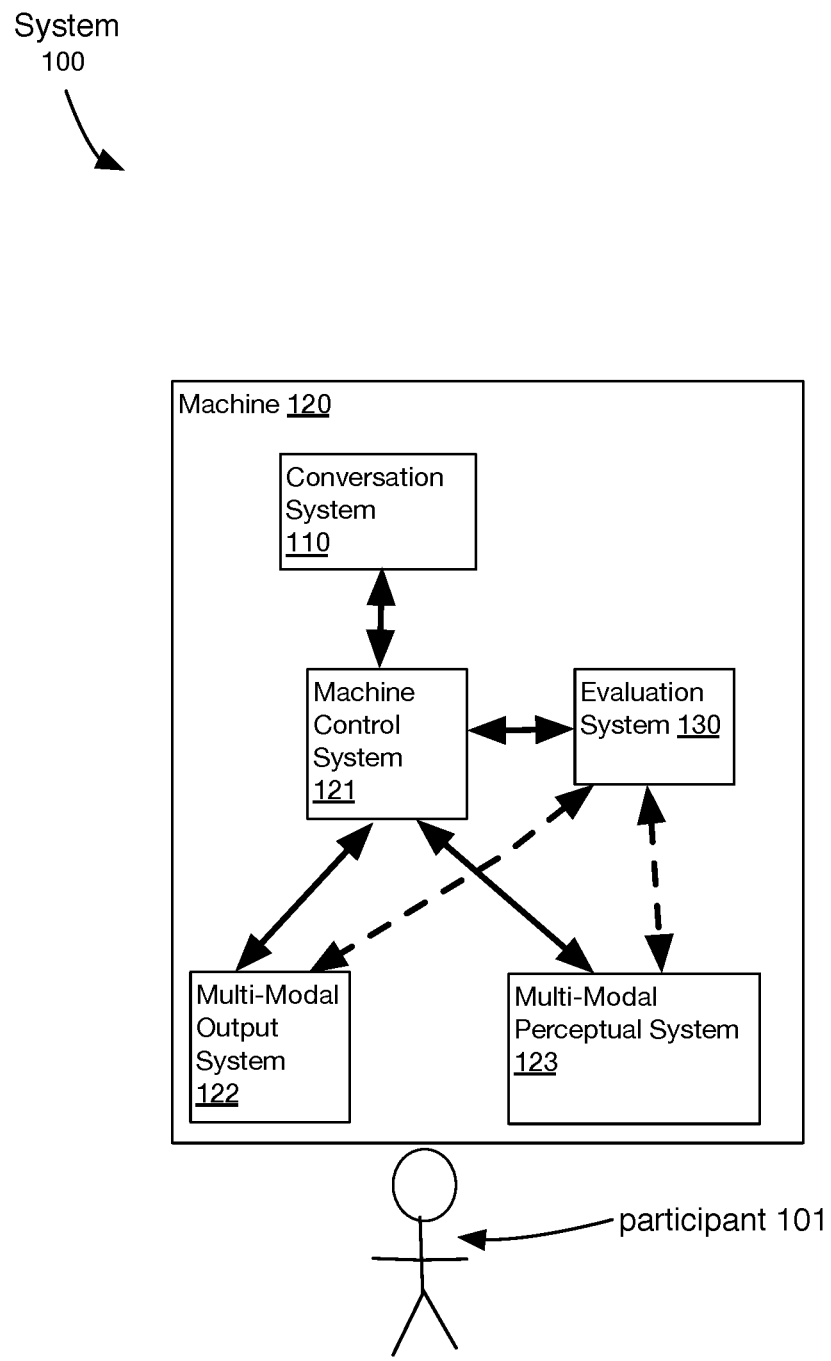
Figure 1C:
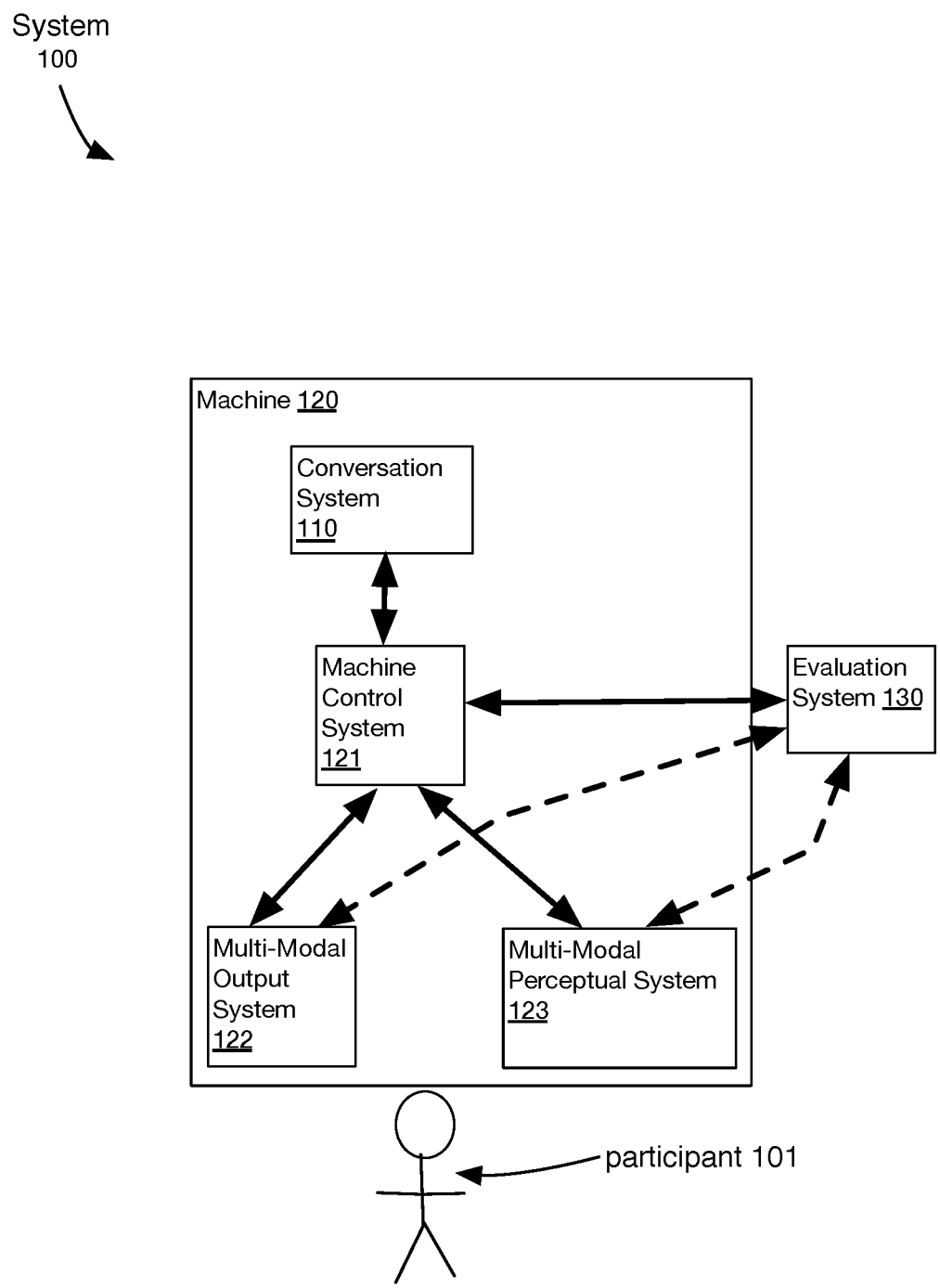
Figure 1D:
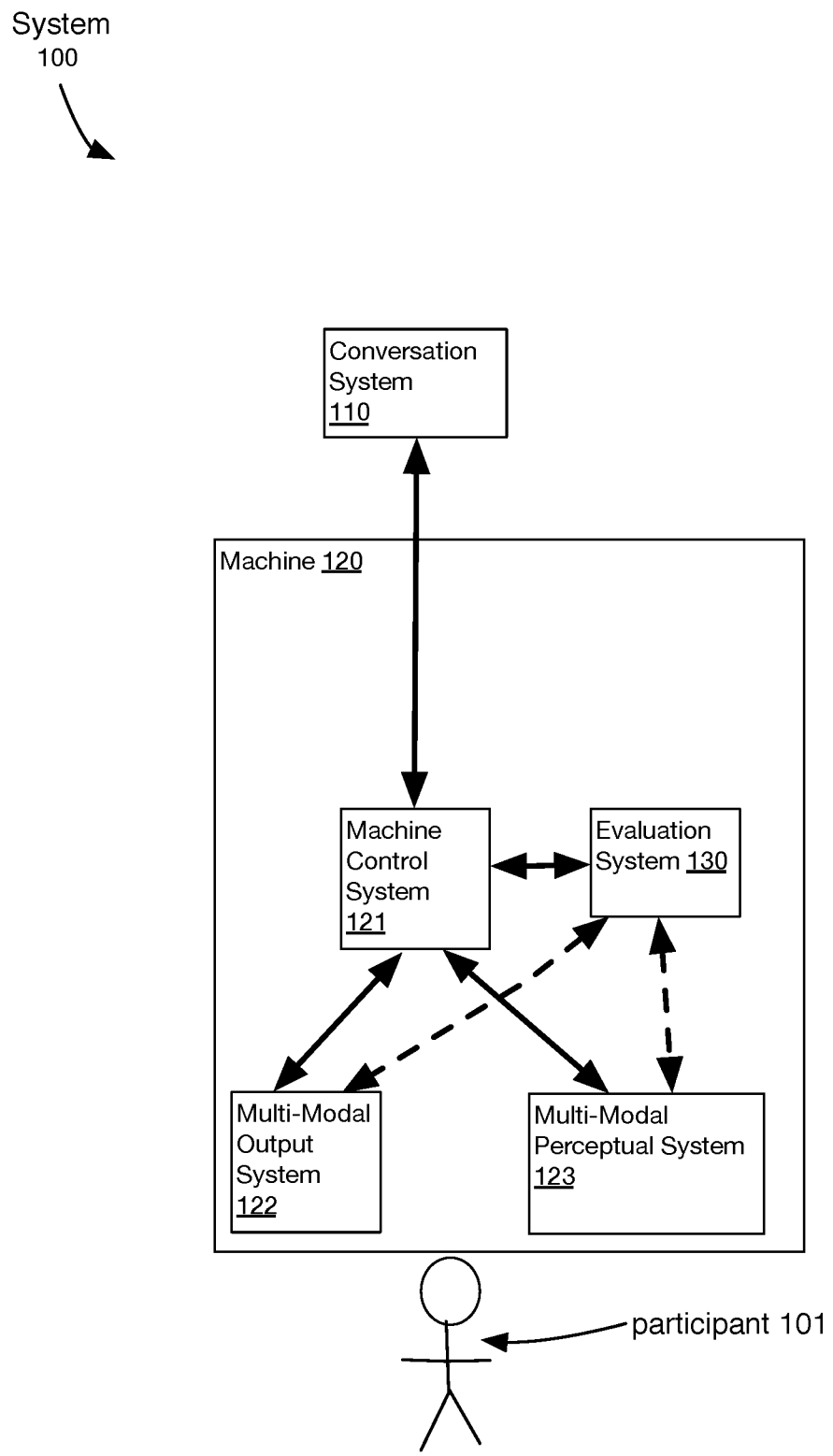
Figure 1E:
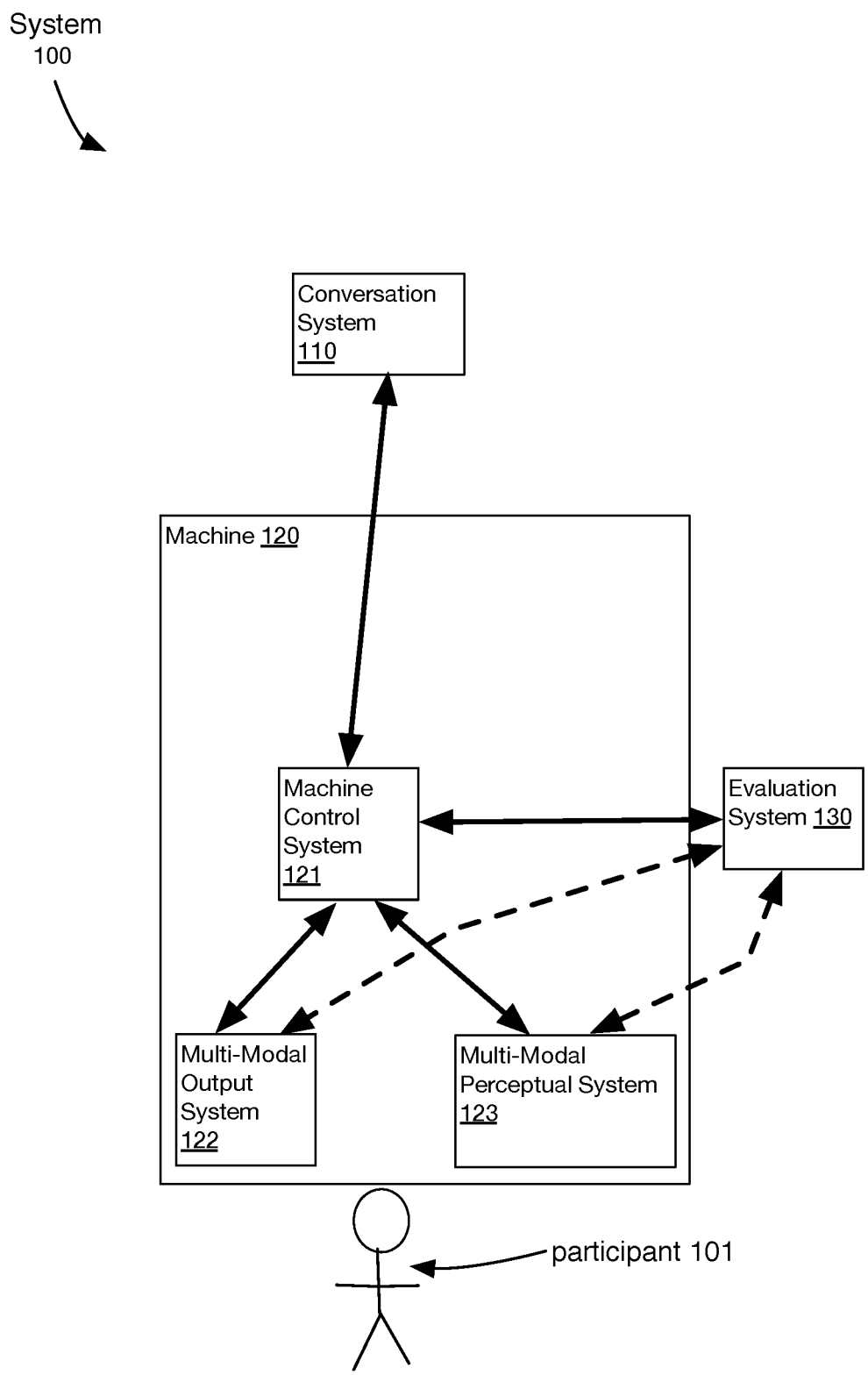

The following description of embodiments is not intended to limit the disclosure to these embodiments, but rather to enable any person skilled in the art to make and use the embodiments disclosed herein.

Overview

Embodiments herein include systems and methods relating to using a machine to interact with at least one human participant by using multi-modal output capabilities of the machine, using an evaluation system coupled to at least one sensor to assess behavior of the human participant during interaction with the machine, and adapting the machine's interaction with the participant based on the assessed human behavior. In some embodiments, the machine is a robot.

Example use cases of such systems and methods include using the machine to: 1) provide therapy to a human participant, 2) provide skill-based training to a human, 3) provide a medical evaluation to a human, 4) provide physical therapy to a human, 5) provide physical athletic training to a human, 6) provide machine-assisted casting by evaluating a human's suitability to perform a specific dramatic role, 7) evaluate a job candidate's suitability for a particular job function. Other uses cases that benefit from systems and methods disclosed herein are also contemplated.

Conversation System

In some embodiments, machine interaction via the machine's multi-modal output system is controlled by a conversation system. The conversation system controls the machine's interaction with the human participant in accordance with conversational content that specifies machine output and associated human input. For example, conversational content can include an expression that matches expected human input, and an associated machine output that is to be performed if sensed human input matches the expression. In some embodiments, the conversation system is similar to the PullString® conversation system. In some embodiments, the conversation system is the Embodied Chat Operating System. In some embodiments, the Embodied Chat Operating System is similar to the PullString® conversation system.

Multi-Modal Output

In some embodiments, the machine includes a multi-modal output system that is constructed to provide the multi-modal output of the machine. For example, in the case of a robotic machine, the multi-modal output system can include a mechanical arm assembly that can be controlled to perform interactive gestures, a speaker to output sound, and a robotic head assembly that includes a face-like display screen that can be controlled to display images corresponding to facial expressions; multi-modal output of such a machine would include arm gestures, sounds and displayed facial expressions, either individually or in combination. In some embodiments, the facial expressions are human-like facial expressions.

As described above, the multi-modal output of the machine is performed in accordance with the conversational content. For example, if the conversational content includes a command to perform a greeting, then the conversation system controls the machine to provide multi-modal output that corresponds to a greeting. Such a greeting can be, for example, an arm wave, controlling the speaker to play audio that corresponds to the spoken word "Hello!", controlling a robotic head to make eye contact with the human participant and display a facial expression corresponding to a greeting. In some embodiments, the greeting command of the conversational content is a general greeting command to have the machine perform multi-modal output of a greeting, in accordance with machine-executable instructions of the machine that correspond to output of a greeting. In some embodiments, the greeting command of the conversational content is a specific greeting command that controls the machine to perform a greeting in a specific manner. For example, a specific greeting command can specify that the machine should greet the human participant by making eye contact, waiving the arm, and saying "Hello!". As another example, a general greeting command can specify that the machine should greet the human participant, and the machine executes instructions of the machine's greeting module to perform the greeting.

Content Authoring

In some embodiments, conversational content is authored by a conversation authoring system. In some embodiments, the conversation authoring system is the PullString® Converse authoring system. In some embodiments, the conversation authoring system is the PullString® Author authoring system.

In some embodiments, the conversation authoring system is the Embodied Chat Operating System. In some embodiments, the Embodied Chat Operating System is similar to the PullString® Converse authoring system. In some embodiments, the Embodied Chat Operating System is similar to the PullString® Author authoring system.

In some embodiments, the conversation authoring system receives user input that specifies machine output, expressions that match expected human input, and relationships between expected human input and responsive machine output. In some embodiments, the conversational content defines a voice user interface. In some embodiments, the authoring system receives user input that specifies non-verbal output to be performed by the machine (e.g., arm gestures, facial expressions, moods to be expressed by the machine, emotions to be expressed by the machine, reactions to be expressed by the machine, and the like). In some embodiments, the authoring system receives user input that selects an existing facial expression image to be output by the machine. In some embodiments, the authoring system receives user input that defines a facial expression image to be output by the machine. In some embodiments, the authoring system specifies other modalities, such as, for example, a LED light ring, a sound, a special effect on the face (e.g., like badges, a star, etc.).

Goal Authoring

In some embodiments, a goal authoring system is provided to define goals for the conversational content. For example, a goal can be "The participant can imitate facial expressions displayed on the robot". In some embodiments, the goal authoring system is used to define goal levels for a goal. For example, for the goal "The participant can imitate facial expressions displayed on the robot", a first goal level can be "The participant can imitate basic emotions such as happy, sad, and angry", a second goal level can be "The participant can imitate secondary emotions such as surprised, afraid, and disgusted", and a third goal level can be "The participant can demonstrate more complex emotions such as embarrassed and shy". In some embodiments, the goal authoring system receives a user instruction that defines a goal level. In some embodiments, the goal authoring system automatically generates at least one goal level for a defined goal (e.g., by using a template, based on known goal levels of similar goals, etc.). In some embodiments, the goal authoring system is used to define participant support levels for a goal level. For example, for the goal level "The participant can imitate basic emotions such as happy, sad, and angry", a first participant support level defines no prompting, whereas a second participant support level provides one prompt, and a third participant level provides 3 prompts; an example prompt can include a command to control the machine to instruct "Try turning down the corners of your mouth into a frown". In some embodiments, the goal authoring system receives a user instruction that defines a participant level. In some embodiments, the goal authoring system automatically generates at least one participant level for a defined goal level (e.g., by using a template, based on known participant levels of similar goals or goal levels, etc.).

In some embodiments, the goal authoring system generates goal definition information that is used to generate conversational content. In some embodiments, the conversation authoring system uses the goal definition information to generate conversational content. In some embodiments, a content creator uses the goal definition information while generating conversational content by using the conversation authoring tool. For example, the content creator uses the conversation authoring system to author content that is designed to evaluate each goal defined in the goal definition information at each defined goal level, and that includes the prompts defined in the goal definition information. In some embodiments, the goal definition information specifies an evaluation module of the machine that is to be used to evaluate a specific goal (e.g., speech recognition module, emotion detection module, client device notification module, etc.)

Conversation Testing

In some embodiments, machine interaction via the machine's multi-modal output system is controlled by a conversation testing system. In some embodiments, the conversation testing system is controlled by a test operator that controls the conversation testing system to provide the machine with multi-modal output instructions; and the conversation testing system receives (from the machine) event information indicating a human response sensed by the machine. In this manner, the test operator can manually provide output instructions of a candidate conversational content being tested and observe the human's response in real-time; based on such observations, the test operator can update the candidate conversational content as needed before finalizing the conversational content for production use.

Assessing Human Behavior

As described herein, an evaluation system assesses the human participant's behavior during interaction with the machine. In some embodiments, the evaluation system assesses the behavior by using at least one sensor. In some embodiments, a sensor used to evaluate human behavior includes a sensor of a heat detection sub-system, a sensor of a video capture sub-system, a sensor of an audio capture sub-system, a touch sensor, a piezoelectric pressor sensor, a capacitive touch sensor, a resistive touch sensor, a blood pressure sensor, a heart rate sensor, and a biometric sensor.

In some embodiments, the evaluation system assesses the behavior by processing information generated by a sensor by using at least one of an emotion detection system, a speech recognition system, a gesture detection system, a voice recognition system, a face detection system, a language recognition system, a behavior recognition system, and an object recognition system.

In some embodiments, the evaluation system assesses the behavior by using information provided by a remote system (e.g., a parent's mobile device, etc.). For example, after an interactive session in which the machine is controlled to teach a child facial expressions for emotions, the evaluation system can send a parent an e-mail or electronic notification via the parent's mobile device asking the parent if the child can now make correct facial expressions for emotions, such as, for example, happy, sad and angry.

In some embodiments, the evaluation system assesses the behavior by using information provided by a second human participant (e.g., a parent, etc.). For example, after an interactive session in which the machine is controlled to teach a child facial expressions for emotions, the evaluation system can control the machine to ask a parent that is present in the same room as the robot if the child can now make correct facial expressions for emotions, such as, for example, happy, sad and angry, and the machine can sense the parent's response by using a sensor.

Conversational Content

In some embodiments, the machine's interaction with the participant is controlled based on conversational content that specifies machine actions to be performed. In some embodiments, at least one goal is defined for the conversational content. In some embodiments, at least one goal level is defined for at least one goal of the conversational content. In some embodiments, at least one participant support level is defined for at least one goal level of the conversational content.

In some embodiments, specific machine actions of the conversational content are associated with a goal, and those machine actions are performed when the associated goal is enabled, whereas those machine actions are not performed when the associated goal is disabled. In some embodiments, specific machine actions of the conversational content are associated with a goal level, and those machine actions are performed when the associated goal level is enabled, whereas those machine actions are not performed when the associated goal level is disabled. In some embodiments, specific machine actions of the conversational content are associated with a participant support level, and those machine actions are performed when the associated participant support level is enabled, whereas those machine actions are not performed when the associated participant support level is disabled.

Adapt Machine Interaction Based on Assessed Human Behavior

In some embodiments, the machine's interaction with the participant is adapted based on the assessed human behavior.

In some embodiments, the machine can increase or decrease an amount of prompting used to elicit a desired human response from the participant based on the assessed behavior of the human participant. If the user is responding successfully, prompting is reduced, whereas if a user is not responding successfully, or is ignoring the machine, prompting is increased. In some embodiments, prompting is increased by enabling a participant support level that defines increased prompting. In some embodiments, prompting is decreased by enabling a participant support level that defines decreased prompting. In some embodiments, prompting is decreased by disabling at least one participant support level.

In some embodiments, the machine performs actions defined for a higher goal level if the user is responding successfully; otherwise, the machine performs actions defined for a lower goal level if the user is not responding successfully.

In some embodiments, the machine performs actions defined for a new goal based on the human participant's behavior. For example, if the participant appears to be bored, then the machine performs actions for a new goal, in hopes of gaining the participant's attention.

In some embodiments, the machine switches to new conversational content based on the human participant's behavior, and performs actions defined for the new conversational content. For example, if the participant appears to be bored, then the machine performs actions for a new conversational content, in hopes of gaining the participant's attention.

Adapt Machine Interaction Based on a Command

In some embodiments, the machine's interaction with the participant is adapted based on a command. In some embodiments, the command is received from an external system (e.g., a parent's smart phone). In some embodiments, the command is recognized from interaction of a participant sensed by the machine. In some embodiments, a parent or teacher in the same room as the machine and a child provides a voice command or gesture to adapt the machine's interaction by at least one of selecting new conversational content, skipping the current conversational content, selecting a new goal, selecting a new goal level, and selecting a new participant support level.

Adapt Machine Interaction Based on Evaluation Results

In some embodiments, the machine's interaction with the participant is adapted based on evaluation results. For example, easier content can be selected based on poor evaluation results, whereas more difficult content can be selected based on successful evaluation results. For example, new content can be selected based successful evaluation results.

Adapt Machine Interaction

In some embodiments, the machine's interaction with the participant is adapted based on content associated with successful evaluation results of similar participants. For example, if the user is not responding successfully, the content can be updated to include machine actions of similar content that has resulted in positive results from similar participants.

In some embodiments, the machine's interaction with the participant is adapted based on history of previously used conversational content. For example, specific machine actions can be enabled or disabled based on information relating to conversational content previously used during interaction with the human participant.

In some embodiments, the machine's interaction with the participant is adapted based on a conversational content schedule. In some embodiments, a content schedule specifies an order in which conversational content is delivered to the human participant.

Overview of Systems and Methods

Embodiments herein include systems and methods that use a conversation system to control multi-modal output of a machine in accordance with selected content, and that use an evaluation system to update content used by the conversation system to control multi-modal output of the machine-based sensing of a human interaction participant by at least one sensor of the machine. In some embodiments, evaluation results are provided to an external client device based on the sensing of the participant. In some embodiments, the machine provides event information to the conversation system based on sensing of the participant, and the conversation system controls multi-modal output of the machine in accordance with the event information. In some embodiments, the machine provides event information to the conversation system based on sensing of the participant, and the conversation system updates the content based on the event information. In some embodiments, the machine is a robot.

Systems

In some embodiments, at least one method described herein is performed by a system that includes the conversation system 110, a machine control system 121, a multi-modal output system 122, a multi-modal perceptual system 123, and an evaluation system 130 (e.g., system 100 of FIGS. 1A-E). In some embodiments, at least one of the conversation system 110, a machine control system 121, a multi-modal output system 122, a multi-modal perceptual system 123, and an evaluation system 130 is included in a machine. In some embodiments, the machine is a robot.

In some embodiments, the conversation system 110 is communicatively coupled to a control system 121 of the machine. In some embodiments, the conversation system 110 is communicatively coupled to the evaluation system 130. In some embodiments, the conversation system 110 is communicatively coupled to a conversational content repository 140. In some embodiments, the conversation system 110 is communicatively coupled to a conversation testing system 150. In some embodiments, the conversation system 110 is communicatively coupled to a conversation authoring system 160. In some embodiments, the conversation system 110 is communicatively coupled to a goal authoring system 170.

In some embodiments, the conversation system 110 is a cloud-based conversation system provided by a conversation system server that is communicatively coupled to the control system 121 via the Internet. In some embodiments, the conversation system 110 is similar to a PullString conversation system. In some embodiments, the conversation system is the Embodied Chat Operating System. In some embodiments, the Embodied Chat Operating System is similar to the PullString® conversation system. In some embodiments, the conversation system 110 is an embedded conversation system that is included in the machine.

In some embodiments, the control system 121 is constructed to control a multi-modal output system 122 and a multi-modal perceptual system 123 that includes the at least one sensor. In some embodiments, the control system 121 is constructed to interact with the conversation system 110.

In some embodiments, the machine includes the multi-modal output system 122. In some embodiments, the multi-modal output system 122 includes at least one of an audio output sub-system, a video display sub-system, a mechanical robotic sub-system, a light emission sub-system, a LED (Light Emitting Diode) ring, and a LED (Light Emitting Diode) array.

In some embodiments, the machine includes the 123 multi-modal perceptual system 123, wherein the multi-modal perceptual system 123 includes the at least one sensor. In some embodiments, the multi-modal perceptual system 123 includes at least one of a sensor of a heat detection sub-system, a sensor of a video capture sub-system, a sensor of an audio capture sub-system, a touch sensor, a piezoelectric pressor sensor, a capacitive touch sensor, a resistive touch sensor, a blood pressure sensor, a heart rate sensor, and a biometric sensor.

In some embodiments, the evaluation system 130 is communicatively coupled to the control system 121. In some embodiments, the evaluation system 130 is communicatively coupled to the multi-modal output system 122. In some embodiments, the evaluation system 130 is communicatively coupled to the multi-modal perceptual system 123. In some embodiments, the evaluation system 130 is communicatively coupled to the conversation system 110. In some embodiments, the evaluation system 130 is communicatively coupled to a client device 190 (e.g., a parent or guardian's mobile device). In some embodiments, the evaluation system 130 is communicatively coupled to the goal authoring system 170.

In some embodiments, the evaluation system 130 includes machine-executable instructions of a goal evaluation module that, when executed by the evaluation system, control the evaluation system to process information generated from the multi-modal perceptual system 123 to evaluate a goal associated with conversational content processed by the conversation system 110. In some embodiments, the goal evaluation module is generated based on information provided by the goal authoring system 170. In some embodiments, the goal evaluation module is generated based on information provided by the conversation authoring system 160. In some embodiments, the goal evaluation module is generated by an evaluation module generator 193.

In some embodiments, the conversation testing system 150 receives user input from a test operator and provides the control system 121 with multi-modal output instructions (either directly or via the conversation system no). In some embodiments, the conversation testing system 150 receives event information indicating a human response sensed by the machine (either directly from the control system 121 or via the conversation system no).

In some embodiments, the conversation authoring system 160 is constructed to generate conversational content and store the conversational content in one of the content repository 140 and the conversation system 110. In some embodiments, responsive to updating of content currently used by the conversation system 110, the conversation system is constructed to store the updated content at the content repository 140.

In some embodiments, the goal authoring system 170 is constructed to generate goal definition information that is used to generate conversational content. In some embodiments, the goal authoring system 170 is constructed to store the generated goal definition information in a goal repository 180. In some embodiments, the goal authoring system 170 is constructed to provide the goal definition information to the conversation authoring system 160.

In some embodiments, the goal authoring system 170 provides a goal definition user interface to a client device that includes fields for receiving user-provided goal definition information. In some embodiments, the goal definition information specifies a goal evaluation module that is to be used to evaluate the goal. In some embodiments, each goal evaluation module is at least one of a sub-system of the evaluation system 130 and a sub-system of the multi-modal perceptual system 123. In some embodiments, each goal evaluation module uses at least one of a sub-system of the evaluation system 130 and a sub-system of the multi-modal perceptual system 123. In some embodiments, the goal authoring system 170 is constructed to determine available goal evaluation modules by communicating with the machine, and update the goal definition user interface to display the determined available goal evaluation modules.

In some embodiments, the goal definition information defines goal levels for a goal. In some embodiments, the goal authoring system 170 defines the goal levels based on information received from the client device (e.g., user-entered data provided via the goal definition user interface). In some embodiments, the goal authoring system 170 automatically defines the goal levels based on a template. In some embodiments, the goal authoring system 170 automatically defines the goal levels based information provided by the goal repository 180, which stores information of goal levels defined form similar goals.

In some embodiments, the goal definition information defines participant support levels for a goal level. In some embodiments, the goal authoring system 170 defines the participant support levels based on information received from the client device (e.g., user-entered data provided via the goal definition user interface). In some embodiments, the goal authoring system 170 automatically defines the participant support levels based on a template. In some embodiments, the goal authoring system 170 automatically defines the participant support levels based information provided by the goal repository 180, which stores information of participant support levels defined form similar goal levels.

In some embodiments, conversational content includes goal information indicating that a specific goal should be evaluated, and the conversational system 110 provides an instruction to the evaluation system 130 (either directly or via the control system 12) to enable the associated goal evaluation module at the evaluation system 130. In a case where the goal evaluation module is enabled, the evaluation system 130 executes the instructions of the goal evaluation module to process information generated from the multi-modal perceptual system 123 and generate evaluation information. In some embodiments, the evaluation system 130 provides generated evaluation information to the conversation system 110 (either directly or via the control system 121). In some embodiments, the evaluation system 130 updates the current conversational content at the conversation system 110 or selects new conversational content at the conversation system 100 (either directly or via the control system 121), based on the evaluation information.

In some embodiments, the machine 120 includes the conversation system and the evaluation system (FIG. 1B), and the machine performs at least one method described herein.

In some embodiments, the machine 120 includes the conversation system (FIG. 1C), and at least one method described herein is performed by a system that includes the machine and the evaluation system.

In some embodiments, the machine 120 includes the evaluation system (FIG. 1D), and at least one method described herein is performed by a system that includes the machine and the conversation system.

In some embodiments, the machine 120 includes the control system 121 (FIG. 1E), and at least one method described herein is performed by a system that includes the machine, the conversation system, and the evaluation system.

In some embodiments, the system 100 includes a goal evaluation module generator 193 that is constructed to generate goal evaluation modules used by the evaluation system 130.

Figure 1F:
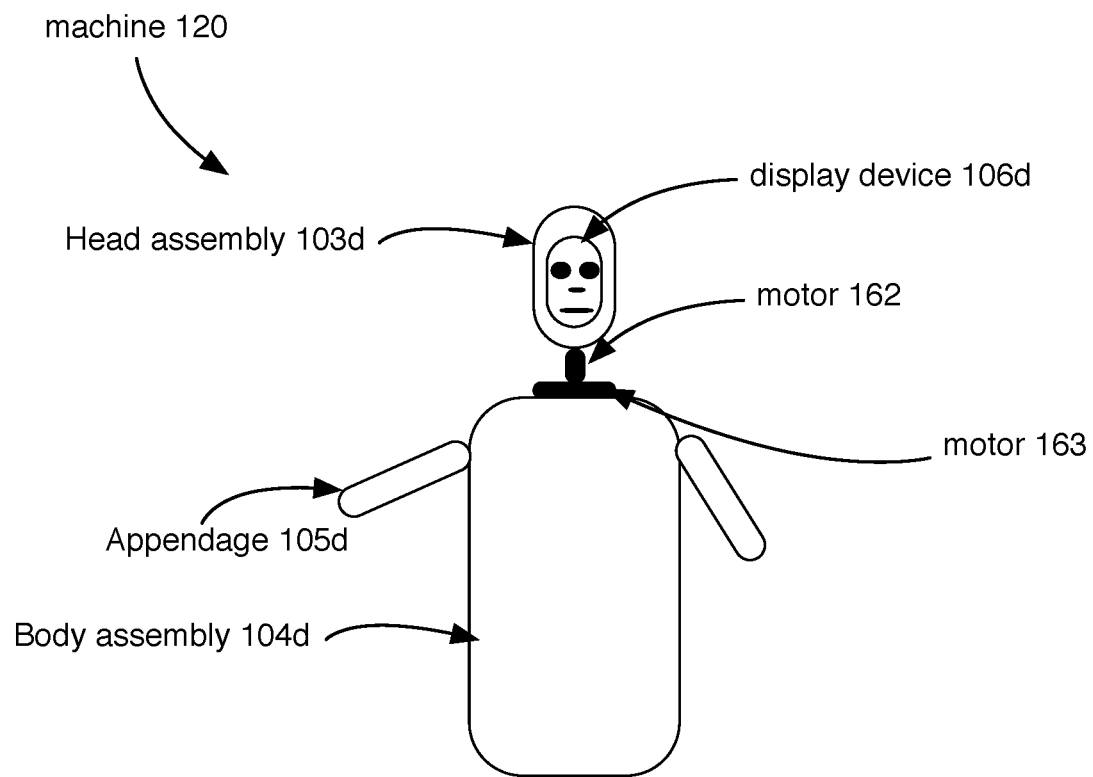

In some embodiments, the machine 120 is a robot. In some embodiments, as shown in FIG. 1F, the robot 120 includes a head assembly 103d, a display device 106d, at least one mechanical appendage 105d, a body assembly 104d, a vertical axis rotation motor 163, and a horizontal axis rotation motor 162. In some embodiments, the robot 120 includes the multi-modal output system, the multi-modal perceptual system 123 and the control system 121.

Content Selection

In some embodiments, the machine is constructed to select the content.

In some embodiments, the control system is constructed to select the content.

In some embodiments, the evaluation system is constructed to select the content.

In some embodiments, a content scheduler of the machine is constructed to select the content.

In some embodiments, the content is selected based on at least one of: sensing of the human interaction participant by using the perceptual system 123; evaluation results of the evaluation system; content associated with successful evaluation results of similar participants; history of previously used conversational content; history of previously used conversational content and related evaluation results; a specified conversational content schedule; and a content selection instruction received from an external system.

In some embodiments, new content is selected based on at least one of: sensing of the human interaction participant by using the perceptual system 123; evaluation results of the evaluation system; content associated with successful evaluation results of similar participants; history of previously used conversational content; history of previously used conversational content and related evaluation results; a specified conversational content schedule; and a content selection instruction received from an external system.

In some embodiments, easier content is selected based on poor evaluation results, whereas more difficult content is selected based on successful evaluation results. In this manner, content is adaptively selected based on the participant's sensed activity.

In some embodiments, new content is selected based on sensing (by using at least on sensor of the machine) that the human interaction participant is not interacting with the current content.

In some embodiments, new content is selected in response to the machine receiving a content selection instruction from an external system (e.g., a parent's mobile device, an operator device, etc.)

In some embodiments, new content is selected in response to the machine receiving a content skip instruction from an external system (e.g., a parent's mobile device, an operator device, etc.).

Content

In some embodiments, the selected conversational content specifies at least a first machine output and at least a first participant input associated with the first machine output. In some embodiments, at least one output of the selected content is a conditional output that is associated with a goal. In some embodiments, at least one output of the selected content is a conditional output that is associated with a goal level. In some embodiments, at least one output of the selected content is a conditional output that is associated with a participant support level.

In some embodiments, the goal definition information generated by the goal authoring system is used to associate conditional output of the conversational content with at least one of a goal, a goal level, and a participant support level.

In some embodiments, the conversation authoring system users the goal definition information generated by the goal authoring system to associate conditional output of the conversational content with at least one of a goal, a goal level, and a participant support level, in accordance with goal, goal level and participant support level definitions of the goal definition information.

Conditional Output

In some embodiments, the conversation system is constructed to process a conditional output of the selected conversational content in response to a determination that an associated goal is enabled.

In some embodiments, the conversation system is constructed to process a conditional output of the selected conversational content in response to a determination that an associated goal level is enabled.

In some embodiments, the conversation system is constructed to process a conditional output of the selected conversational content in response to a determination that an associated participant support level is enabled.

Select Enablement of Goals, Goal Levels, and Support Levels

In some embodiments a goal, a goal level, and a participant support level of a current interaction session are selectively enabled. In some embodiments, the machine selectively enables at least one of a goal, a goal level, and a participant support level of a current interaction session. In some embodiments, the control system selectively enables at least one of a goal, a goal level, and a participant support level of a current interaction session. In some embodiments, the evaluation system selectively enables at least one of a goal, a goal level, and a participant support level of a current interaction session. In some embodiments, an external system selectively enables at least one of a goal, a goal level, and a participant support level of a current interaction session.

Goals

In some embodiments, a goal is selectively enabled (or disabled) based on at least one of: sensing of the human interaction participant by using the perceptual system 123; evaluation results of the evaluation system; content associated with successful evaluation results of similar participants; history of previously used conversational content; history of previously used conversational content and related evaluation results; a specified conversational content schedule; and an instruction received from an external system.

In some embodiments, an easier goal is enabled (and a current goal disabled) based on poor evaluation results of the current goal, whereas a more difficult goal is enabled based on successful evaluation results. In this manner, goals are adaptively enabled based on the participant's sensed activity.

In some embodiments, a new goal is enabled (and a current goal disabled) based on sensing (by using at least on sensor of the machine) that the human interaction participant (e.g., 101 of FIG. 1A) is not interacting with the conversational content for the current goal.

In some embodiments, a new goal is enabled (and a current goal disabled) in response to the machine receiving a goal selection instruction from an external system (e.g., a parent's mobile device, an operator device, etc.).

In some embodiments, a new goal is enabled (and a current goal disabled) in response to the machine receiving a goal skip instruction from an external system (e.g., a parent's mobile device, an operator device, etc.).

Goal Levels

In some embodiments, a goal level is selectively enabled (or disabled) based on at least one of: sensing of the human interaction participant by the perceptual system 123; evaluation results of the evaluation system; content associated with successful evaluation results of similar participants; history of previously used conversational content; history of previously used conversational content and related evaluation results; a specified conversational content schedule; and an instruction received from an external system.

In some embodiments, an easier goal level is enabled (and a current goal level disabled) based on poor evaluation results of the current goal level, whereas a more difficult goal level is enabled based on successful evaluation results. In this manner, goal levels are adaptively enabled based on the participant's sensed activity.

In some embodiments, a new goal level is enabled (and a current goal level disabled) based on sensing (by using at least on sensor of the machine) that the human interaction participant is not interacting with the conversational content for the current goal level.

In some embodiments, a new goal level is enabled (and a current goal level disabled) in response to the machine receiving a goal level selection instruction from an external system (e.g., a parent's mobile device, an operator device, etc.).

In some embodiments, a new goal level is enabled (and a current goal level disabled) in response to the machine receiving a goal level skip instruction from an external system (e.g., a parent's mobile device, an operator device, etc.).

Support Levels

In some embodiments, a participant support level is selectively enabled (or disabled) based on at least one of: sensing of the human interaction participant by using the perceptual system 123; evaluation results of the evaluation system; content associated with successful evaluation results of similar participants; history of previously used conversational content; history of previously used conversational content and related evaluation results; a specified conversational content schedule; and an instruction received from an external system.

In some embodiments, an easier support level (e.g., a support level with more prompting) is enabled (and a current support level disabled) based on poor evaluation results at the current support level, whereas a more difficult support level (e.g., a support level with less prompting) is enabled based on successful evaluation results. In this manner, support levels are adaptively enabled based on the participant's sensed activity.

In some embodiments, a new support level is enabled (and a current support disabled) based on sensing (by using at least on sensor of the machine) that the human interaction participant is not interacting with the conversational content at the current support level.

In some embodiments, a new support level is enabled (and a current support level disabled) in response to the machine receiving a support level selection instruction from an external system (e.g., a parent's mobile device, an operator device, etc.).

In some embodiments, a new support level is enabled (and a current support level disabled) in response to the machine receiving a support level disable instruction from an external system (e.g., a parent's mobile device, an operator device, etc.).

Content: Use Cases

In some embodiments, the selected conversational content relates to therapy and the evaluation results relate to an assessment of the participant's responsiveness to the therapy.

In some embodiments, the selected conversational content relates to skill-based training and the evaluation results relate to an evaluation of the participant's skills.

In some embodiments, the selected conversational content relates to medical evaluation and the evaluation results relate to an evaluation of the participant's health.

In some embodiments, the selected conversational content relates to physical therapy and the evaluation results relate to an evaluation of the participant's progress in physical therapy.

In some embodiments, the selected conversational content relates to physical training and the evaluation results relate to an evaluation of the participant's progress in physical training.

In some embodiments, the selected conversational content relates to medical evaluation and the evaluation results relate to an evaluation of the participant's health.

In some embodiments, the selected conversational content relates to dramatic casting and the evaluation results relate to an evaluation of the participant's ability to perform a dramatic performance in accordance with specified dramatic goals.

In some embodiments, the selected conversational content relates to a job interview and the evaluation results relate to an evaluation of the participant's ability to perform specified job function.

Content Generation and Goal Generation

In some embodiments, the conversation authoring system 160 generates the selected conversational content based on user-input received via a user input device (e.g., an input device of an operator's computer, mobile device, etc.). In some embodiments, the conversation system includes the conversation authoring system 160. In some embodiments, the conversation authoring system 160 is external to the conversation system. In some embodiments, the conversation authoring system 160 stores and manages a set of goals. In some embodiments, the conversation authoring system 160 stores and manages a set of goals levels for at least one goal managed by the conversation authoring system 160.

Authored Goals

In some embodiments, the conversational content includes at least one conversation output (to be performed by the machine) that is used to evaluate a specified goal defined by the goal definition information. Such a goal that is to be evaluated by a human participant's response to the associated conversational output is referred to herein as an authored goal. In some embodiments, the evaluation system 130 generates information indicating goal success for an authored goal based on a determination that a participant response sensed by the at least one sensor of the machine matches an expected response as defined by the associated conversational content. In some embodiments, the conversation system 110 determines goal success for an authored goal based on a determination that a participant response sensed by the at least one sensor of the machine matches an expected response as defined by the associated conversational content. In some embodiments, the conversation system 110 determines goal success for an authored goal based on a determination that a participant response sensed by the at least one sensor of the machine matches an expected response as defined by the associated conversational content, and provides information indicating goal success to the evaluation system 130. In some embodiments, the conversation system 110 determines goal success for an authored goal based on a determination that a participant response sensed by the at least one sensor of the machine matches an expected response as defined by the associated conversational content, and provides information indicating goal success to the evaluation system 130, and the evaluation system 130 uses the information indicating goal success that is provided by the conversation system to provide evaluation results to a client device (e.g., the client device 190 of FIG. 1A).

Ubiquitous Goals

In some embodiments, the goal definition information defines a ubiquitous goal, which is a goal that is evaluated regardless of the conversational content currently being processed by the conversation system no. For example, a ubiquitous goal could be for a participant to make eye contact with the machine, during interaction, regardless of the conversational content being used. In some embodiments, a ubiquitous goal can evaluated even when conversational content is not being executed by the conversational system, and a ubiquitous goal can be evaluated during a time period in which several different items of conversational content are being executed by the conversational system 110.

In some embodiments, the evaluation system 130 generates information indicating goal success (of a ubiquitous goal) based on a determination that a participant's behavior as sensed by the at least one sensor matches an expected behavior. In some embodiments, the evaluation system 130 determines the expected behavior based on information received from at least one external system (e.g., another machine, a data repository, an operator's client device, etc.). In some embodiments, the evaluation system 130 determines the expected behavior based on information indicating behavior of similar participants during similar contexts.

In some embodiments, the evaluation system 130 evaluates a ubiquitous goal by providing a goal evaluation request to an external system (e.g., 190), receiving a goal evaluation result from the external system, and generating information indicating goal success (of a ubiquitous goal) based on the evaluation result received from the external system. In some embodiments, the evaluation system sends a message (e.g., via SMS, MMS, Push Notifications, e-mail, in-app notification, etc.) to a client device (e.g., a mobile device of a parent of the human participant) requesting information indicating whether the participant has successfully achieved a specified goal (e.g., "yes" or "no"), receives from the client device information indicating whether the participant has successfully achieved the specified goal, and uses the received information to generate the information indicating goal success.

Methods

Method 200

Figure 2:
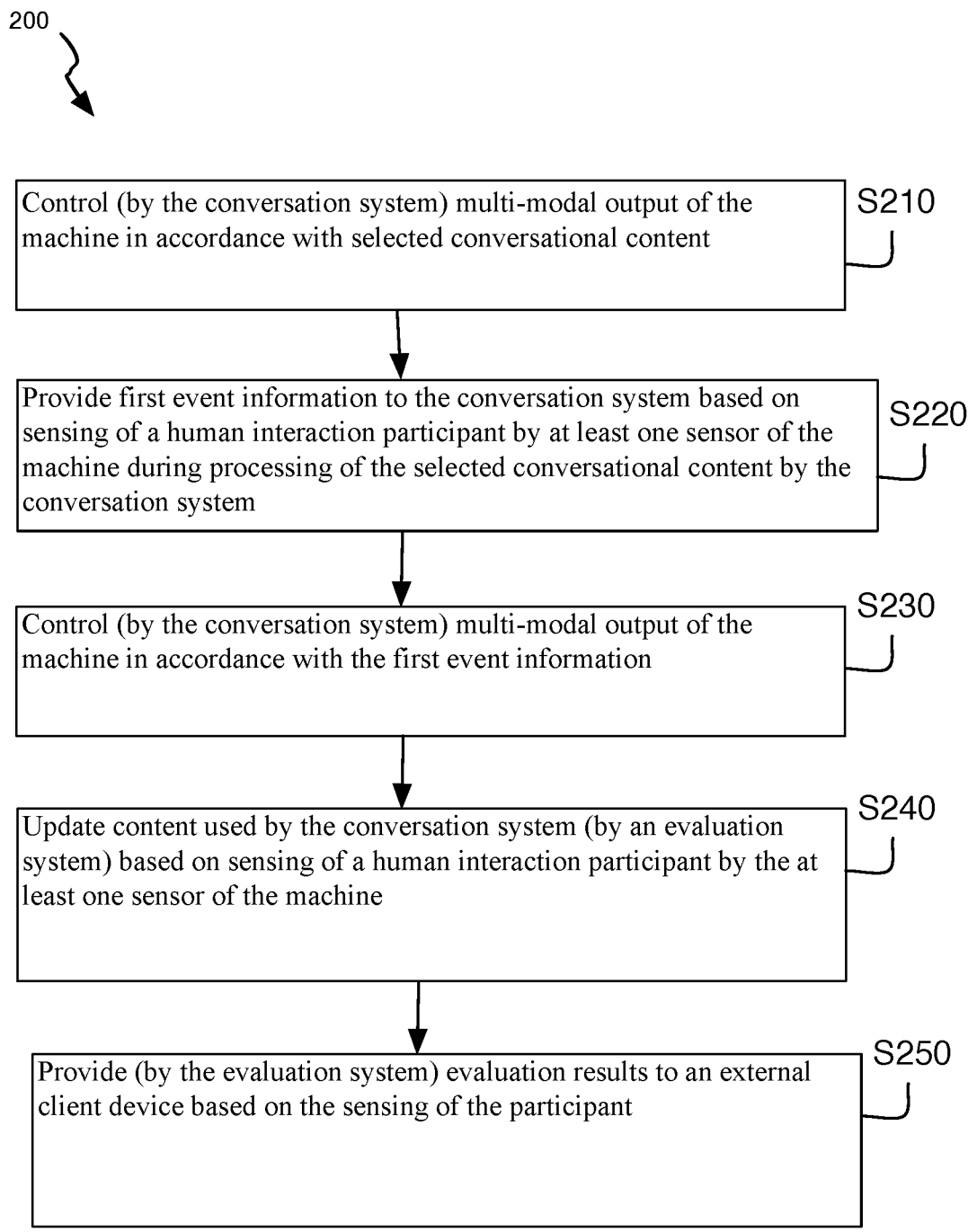
FIG. 2 is a representation of a method, according to embodiments.

FIG. 2 is a representation of a method 200 according to embodiments. In some embodiments, at least one of the conversation system 110, the machine 120, the evaluation system 130, and the control system 121 performs the method 200.

In some embodiments, the method 200 includes: a conversation system (e.g., 110) controlling multi-modal output of the machine (e.g., 120) in accordance with selected conversational content (process S210); a control system (e.g., 121) providing first event information to the conversation system based on sensing of a human interaction participant by at least one sensor of the machine (e.g., a sensor of the multi-modal perceptual system 123) during processing of the selected conversational content by the conversation system (process S220); the conversation system controlling multi-modal output of the machine in accordance with the first event information (process S230); an evaluation system (e.g., 130) updating content used by the conversation system based on sensing of a human interaction participant by the at least one sensor of the machine (process S240); and the evaluation system providing evaluation results to an external client device (e.g., 190) based on the sensing of the participant.

In some embodiments, the method 200 includes the conversation system 110 performing a first conversation behavior associated with second event information received from the control system 121, in accordance with the selected conversational content.

In some embodiments, the selected conversational content specifies at least a first machine output and at least a first participant input associated with the first machine output, and at least one output of the selected content is a conditional output that is associated with at least one of a goal, a goal level, and a participant support level.

Selecting and Updating Content

In some embodiments, the method 200 includes at least one of the control system 121 and the evaluation system 130 selecting the selected conversational content based on at least one of: sensing of the human interaction participant by using the perceptual system 123; evaluation results of the evaluation system; content associated with successful evaluation results of similar participants; history of previously used conversational content; history of previously used conversational content and related evaluation results; a specified conversational content schedule; and a content selection instruction received from an external system (e.g., 190).

In some embodiments, the method includes the evaluation system 130 updating the content based on at least one of: sensing of the human interaction participant by using the perceptual system 123; evaluation results of the evaluation system; content associated with successful evaluation results of similar participants; history of previously used conversational content; history of previously used conversational content and related evaluation results; a specified conversational content schedule; and a content selection instruction received from an external system (e.g., 190).

Enabling Goals, Goal Levels, and Support Levels

In some embodiments, the method 200 includes: at least one of the control system 121 and the evaluation system 130 enabling a goal based on at least one of: sensing of the human interaction participant (by the at least one sensor); evaluation results of the evaluation system; content associated with successful evaluation results of similar participants; history of previously used conversational content; history of previously used conversational content and related evaluation results; a specified conversational content schedule; and an instruction received from an external system.

In some embodiments, the method 200 includes: at least one of the control system 121 and the evaluation system 130 enabling a goal level based on at least one of: sensing of the human interaction participant (by the at least one sensor); evaluation results of the evaluation system; content associated with successful evaluation results of similar participants; history of previously used conversational content; history of previously used conversational content and related evaluation results; a specified conversational content schedule; and an instruction received from an external system.

In some embodiments, the method 200 includes: at least one of the control system 121 and the evaluation system 130 enabling a participant support level based on at least one of: sensing of the human interaction participant (by the at least one sensor); evaluation results of the evaluation system; content associated with successful evaluation results of similar participants; history of previously used conversational content; history of previously used conversational content and related evaluation results; a specified conversational content schedule; and an instruction received from an external system.

In some embodiments, the method 200 includes: at least one of the control system 121 and the evaluation system 130 enabling a participant support level associated with additional participant support, responsive to a determination that the human participant is not successfully completing tasks associated with at least one of an enabled goal and an enabled goal level.

In some embodiments, the method 200 includes: at least one of the control system 121 and the evaluation system 130 enabling a participant support level associated with reduced participant support, responsive to a determination that the human participant is successfully completing tasks associated with at least one of an enabled goal and an enabled goal level.

In some embodiments, the method 200 includes: at least one of the control system 121 and the evaluation system 130 enabling a goal level associated with a reduced difficulty, responsive to a determination that the human participant is not successfully completing tasks associated with at least one of an enabled goal and an enabled goal level.

In some embodiments, the method 200 includes: at least one of the control system 121 and the evaluation system 130 enabling a goal level associated with an increased difficulty, responsive to a determination that the human participant is successfully completing tasks associated with at least one of an enabled goal and an enabled goal level.

In some embodiments, the method 200 includes: at least one of the control system 121 and the evaluation system 130 enabling a new goal, responsive to a determination that the human participant is not successfully completing tasks associated with at least one of an enabled goal and an enabled goal level.

In some embodiments, the method 200 includes: at least one of the control system 121 and the evaluation system 130 enabling a new goal, responsive to a determination that the human participant is successfully completing tasks associated with at least one of an enabled goal and an enabled goal level.

In some embodiments, the method 200 includes: at least one of the control system 121 and the evaluation system 130 enabling a new goal, responsive to a determination that the human participant has successfully completed tasks associated with all goal levels associated with the current goal.

In some embodiments, the method 200 includes: at least one of the control system 121 and the evaluation system 130 enabling a new goal level, responsive to a determination that the human participant has successfully completed tasks associated with the current goal level.

In some embodiments, the method 200 includes: at least one of the control system 121 and the evaluation system 130 enabling a new prompt level, responsive to a determination that the human participant has successfully completed tasks at the current prompt level.

In some embodiments, the evaluation system 130 determines that the human participant has successfully completed a task based on information generated by a sensor of the multi-modal perceptual system 123.

In some embodiments, at least one of the conversation system 110, the machine 120, the evaluation system 130, and the conversational content repository 140 stores information identifying a current goal, a current goal level, and a current participant support level. In some embodiments, at least one of the conversation system 110, the machine 120, the evaluation system 130, and the conversational content repository 140 stores information identifying the current conversational content. In some embodiments, at least one of the conversation system 110, the machine 120, the evaluation system 130, and the conversational content repository 140 stores information identifying a current activity of the current conversational content.

Authoring

In some embodiments, the method 200 includes: a conversation authoring system (e.g., 160) generating the selected conversational content based on user-input received via a user input device and goal definition information generated by a goal authoring system (e.g., 170); and the evaluation system (e.g., 130) evaluating at least one goal defined by the goal definition information during processing of the selected conversational content by the conversational system (e.g., 110).

In some embodiments, the method 200 includes: the goal authoring system (e.g., 170 generating the goal definition information based on user-input received via a user input device.

In some embodiments, the method 200 includes: the goal authoring system providing a user interface to a client device (e.g., 190) (via a network), wherein the user interface (e.g., FIG. 4A) includes at least one field for receiving user-input specifying at least a first goal.

In some embodiments, the method 200 includes: the goal authoring system providing a user interface to a client device (e.g., 190) (via a network), wherein the user interface (e.g., FIG. 4A) includes at least one field for receiving user-input specifying a goal evaluation module of the machine (e.g., a goal evaluation module of the evaluation system 130) that is to be used to evaluate the first goal. In some embodiments, each goal evaluation module of the machine is one of a sub-system of the evaluation system 130 and a sub-system of the multi-modal perceptual system 123.

In some embodiments, the method 200 includes the goal authoring system determining available goal evaluation modules by communicating with the machine 120, and updating the goal definition user interface to display the determined available goal evaluation modules.

In some embodiments, the method 200 includes: the goal authoring system providing a user interface to a client device (e.g., 190) (via a network), wherein the user interface (e.g., FIG. 4B) includes at least one field for receiving user-input specifying at least a first goal level of the first goal.

In some embodiments, the method 200 includes: the goal authoring system providing a user interface to a client device (e.g., 190) (via a network), wherein the user interface (e.g., FIG. 4C) includes at least one field for receiving user-input specifying at least a first participant support level of the first goal level.

In some embodiments, the method 200 includes the goal authoring system 170 automatically defining at least one goal level for the first goal. In some embodiments, the goal authoring system 170 automatically defines the at least one goal level based on a template. In some embodiments, the goal authoring system 170 automatically defines the at least one goal level based on information provided by the goal repository 180, which stores information of goal levels defined form similar goals.

In some embodiments, the method 200 includes the goal authoring system 170 automatically defining at least one participant support level for the first goal level. In some embodiments, the goal authoring system 170 automatically defines the at least one participant support level based on a template. In some embodiments, the goal authoring system 170 automatically defines the at least one participant support level based on information provided by the goal repository 180, which stores information of participant support levels defined form similar goal levels.

FIG. 3 is a schematic representation of exemplary goal definition information 301, according to some embodiments.

Figure 4A:
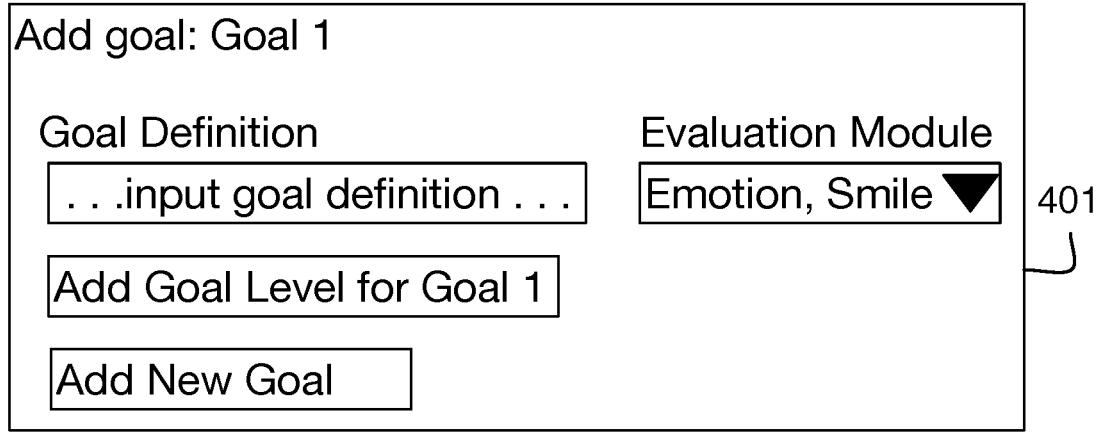
FIGS. 4A-C are representations of user interfaces, according to embodiments.

As shown in FIG. 4A, the user interface 401 includes an input field to receive user input specifying a Goal Definition, an input field to receive a user input selecting at least one evaluation module, a button to add a goal level, and a button to add a new goal. In some embodiments, responsive to receiving user selection of the button to add a new goal level, the goal authoring system 170 provides the client device with a user interface similar to the user interface 402 depicted in FIG. 4B. In some embodiments, responsive to receiving user selection of the button to add a new goal, the goal authoring system 170 updates the user interface of FIG. 4A to include an input field to receive user input specifying a Goal Definition for the new goal, an input field to receive a user input selecting at least one evaluation module for the new goal, a button to add a goal level for the new goal, and a button to add a new goal (e.g., a third goal).

Figure 4B:
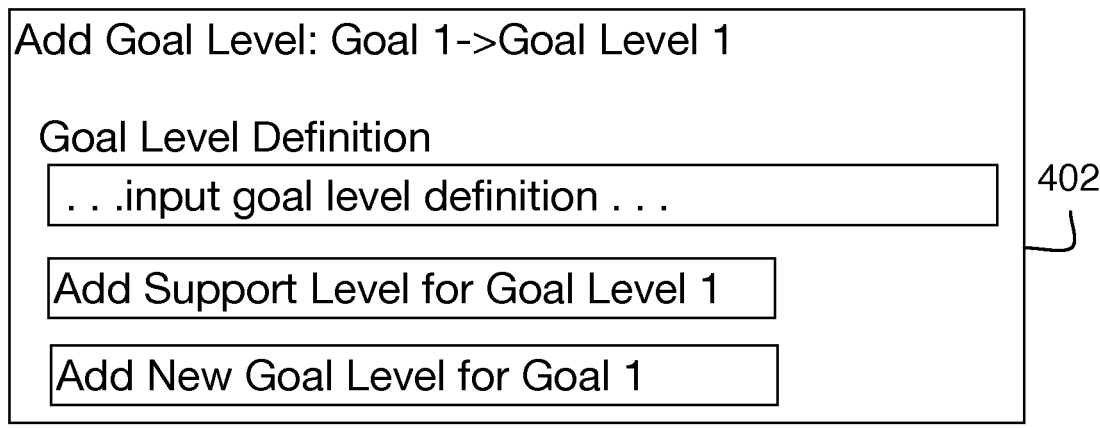

As shown in FIG. 4B, the user interface 402 includes an input field to receive user input specifying a Goal Level Definition, a button to add a support level, and a button to add a new goal level. In some embodiments, responsive to receiving user selection of the button to add a support level, the goal authoring system 170 provides the client device with a user interface similar to the user interface 403 depicted in FIG. 4C. In some embodiments, responsive to receiving user selection of the button to add a new goal level, the goal authoring system 170 updates the user interface of FIG. 4B to include an input field to receive user input specifying a Goal Definition for the new goal level, a button to add a support level for the new goal level, and a button to add a new goal level (e.g., a third goal level).

Figure 4C:
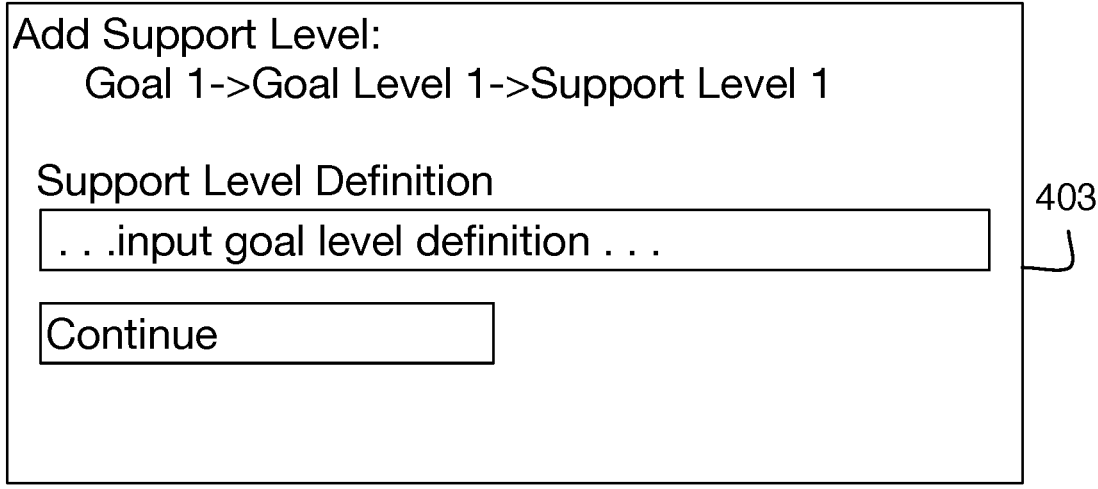

As shown in FIG. 4C, the user interface 403 includes an input field to receive user input specifying a Support Level Definition, and a continue button. In some embodiments, responsive to receiving user selection of the continue button, the goal authoring system 170 provides the client device with the user interface for entering information for a goal level (e.g., a user interface similar to the user interface 402 depicted in FIG. 4B).

Goal Evaluation

In some embodiments, conversational content includes goal information indicating that a specific goal should be evaluated, and the method 200 includes the conversational system 110 providing an instruction to the evaluation system 130 (either directly or via the control system 12) to enable the associated goal evaluation module at the evaluation system 130.

In some embodiments, the method 200 includes: in a case where the goal evaluation module is enabled, the evaluation system 130 executes the instructions of the goal evaluation module to process information generated from the multi-modal perceptual system 123 and generate evaluation information.

In some embodiments, the method 200 includes: the evaluation system 130 providing generated evaluation information to the conversation system 110 (either directly or via the control system 121).

In some embodiments, the method 200 includes: the evaluation system 130 updating the current conversational content at the conversation system 110 (either directly or via the control system 121), based on goal evaluation by the goal evaluation module.

In some embodiments, the method 200 includes: the evaluation system 130 selecting new conversational content at the conversation system 100 (either directly or via the control system 121)), based on goal evaluation by the goal evaluation module.

Testing Content

In some embodiments, the method 200 includes: a conversation testing system (e.g., 150) controlling a multi-modal output system (e.g., 122) of the machine (e.g., 120).

In some embodiments, the method 200 includes: a conversation testing system (e.g., 150) controlling a multi-modal output system (e.g., 122) of the machine (e.g., 120), responsive to user-input received via a user input device of the conversation testing system. In some embodiments, the conversation testing system controls the multi-modal output system by providing multi-modal output instructions to the control system of the machine (e.g., 121) (either directly or via a conversation system, e.g., no) in accordance with the user-input received via the user interface.

In some embodiments, the method 200 includes: the conversation testing system receiving event information from the control system (e.g. 121) (either directly or via a conversation system, e.g., no) indicating a human response sensed by the machine (via the multi-modal perceptual system 123).

In some embodiments, the conversation testing system stores multi-modal output instructions received via the user interface during a test session as a conversational content item (e.g., in the repository 140).

In some embodiments, the test operator manually provides output instructions of candidate conversational content being tested and observes the human's response in real-time; based on such observations, the test operator updates the candidate conversation as needed before finalizing the conversation for production use.

Method 600

Figure 6:
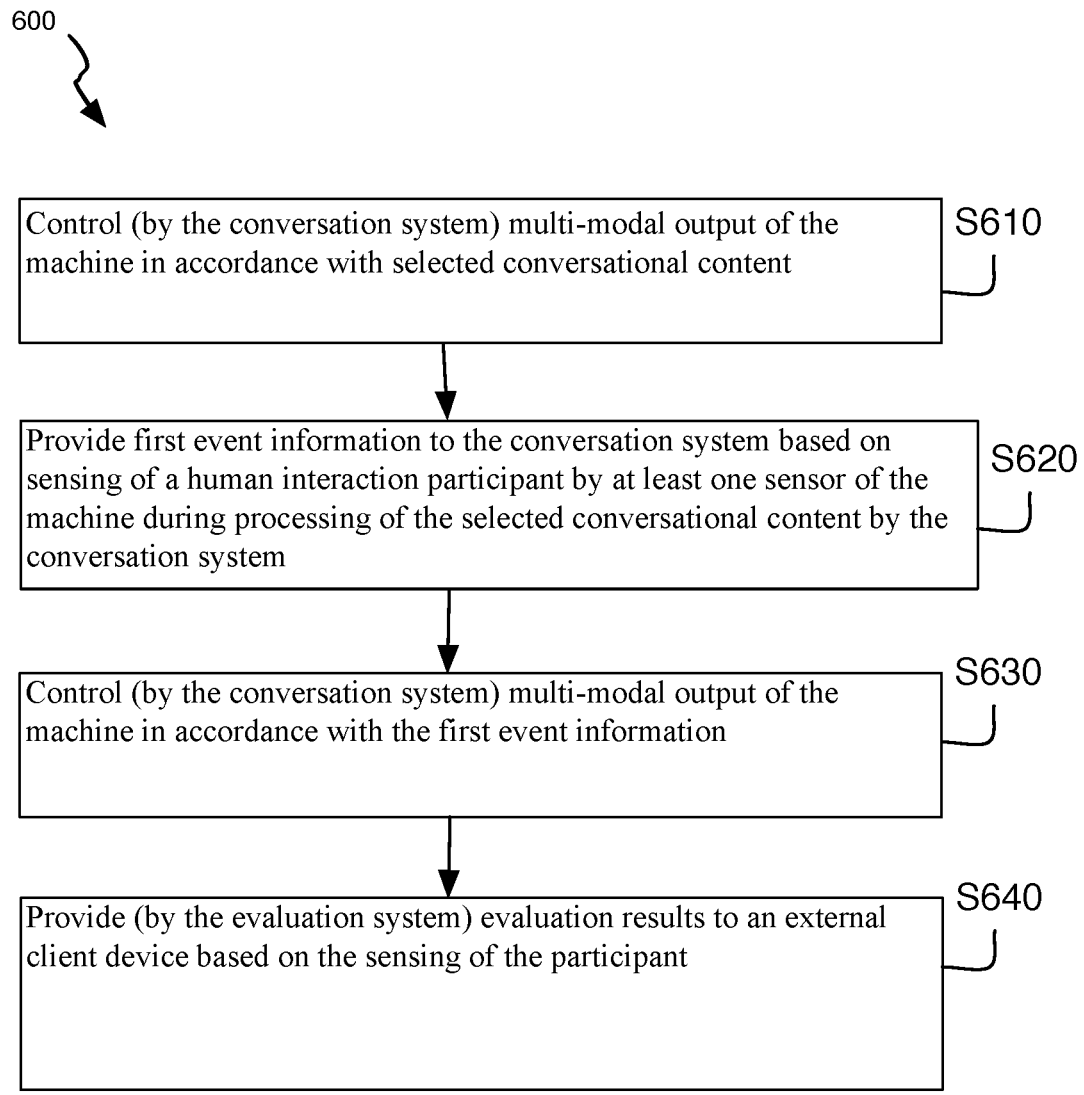
FIGS. 6-9 are representations of methods, according to embodiments.

FIG. 6 is a representation of a method 600 according to embodiments. In some embodiments, at least one of the conversation system 110, the machine 120, the evaluation system 130, and the control system 121 performs the method 600. In some embodiments, at least one of the processes of the method 600 is similar to a process of the method 200.

In some embodiments, the method 600 includes: a conversation system (e.g., 110) controlling multi-modal output of the machine (e.g., 120) in accordance with selected conversational content (process S610); a control system (e.g., 121) providing first event information to the conversation system based on sensing of a human interaction participant by at least one sensor of the machine (e.g., a sensor of the multi-modal perceptual system 123) during processing of the selected conversational content by the conversation system (process S620); the conversation system controlling multi-modal output of the machine in accordance with the first event information (process S630); and an evaluation system providing evaluation results to an external client device (e.g., 190) based on sensing of the human interaction participant by at least one sensor of the machine (process S640).

Method 700

Figure 7:
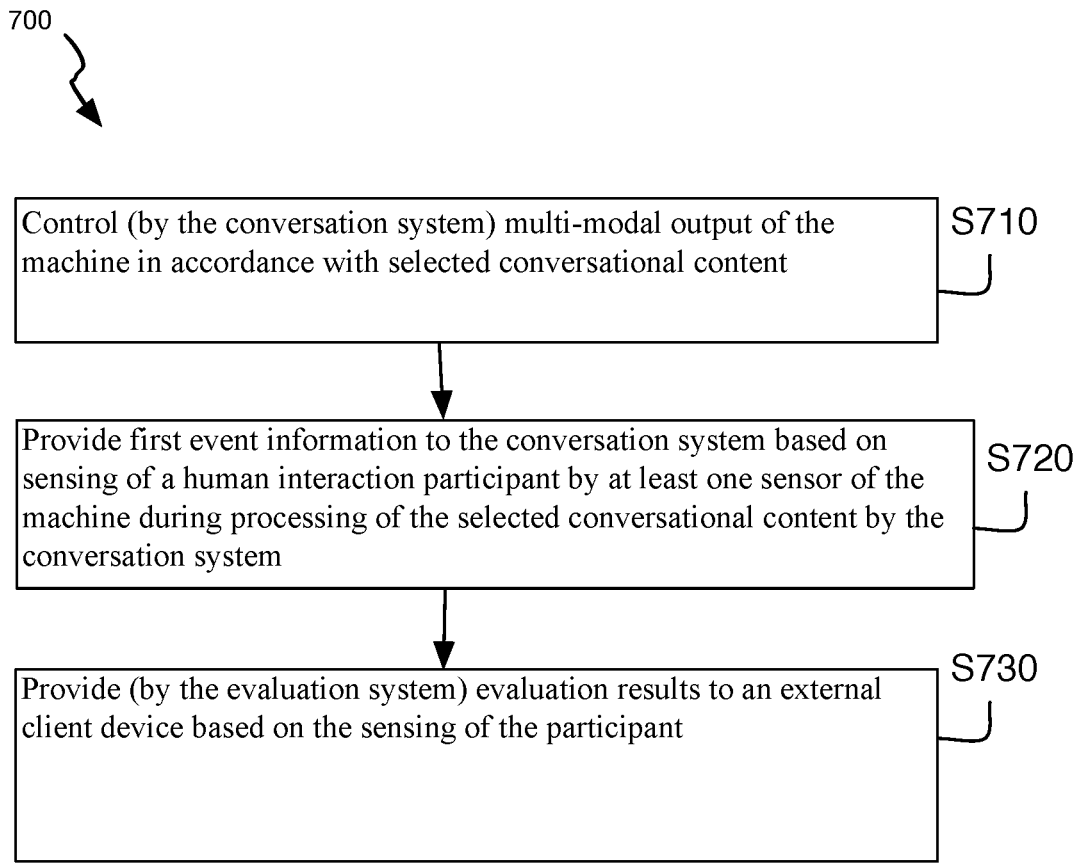

FIG. 7 is a representation of a method 700 according to embodiments. In some embodiments, at least one of the conversation system 110, the machine 120, the evaluation system 130, and the control system 121 performs the method 700. In some embodiments, at least one of the processes of the method 700 is similar to a process of the method 200.

In some embodiments, the method 700 includes: a conversation system (e.g., 110) controlling multi-modal output of the machine (e.g., 120) in accordance with selected conversational content (process S710); a control system (e.g., 121) providing first event information to the conversation system based on sensing of a human interaction participant by at least one sensor of the machine (e.g., a sensor of the multi-modal perceptual system 123) during processing of the selected conversational content by the conversation system (process S720); and an evaluation system providing evaluation results to an external client device (e.g., 190) based on sensing of the human interaction participant by at least one sensor of the machine (process S730).

Method 800

Figure 8:
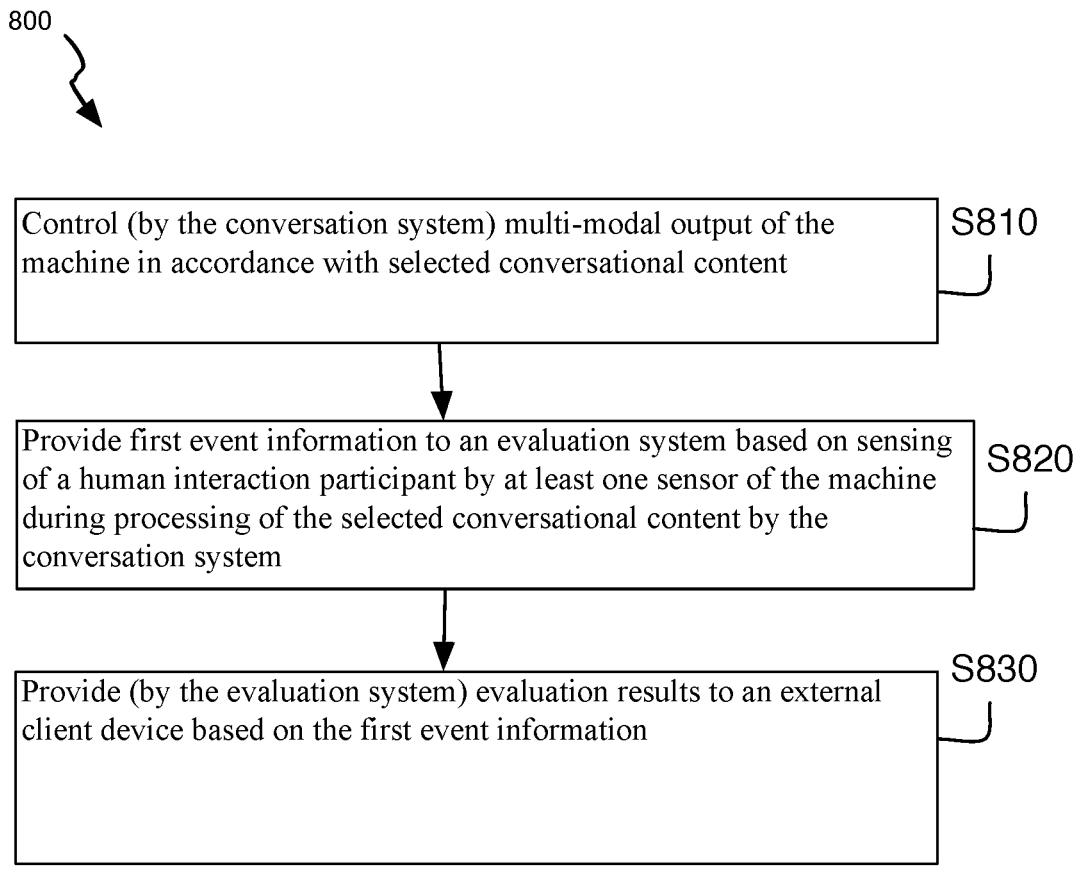

FIG. 8 is a representation of a method 800 according to embodiments. In some embodiments, at least one of the conversation system 110, the machine 120, the evaluation system 130, and the control system 121 performs the method 800. In some embodiments, at least one of the processes of the method 800 is similar to a process of the method 200.

In some embodiments, the method 800 includes: a conversation system (e.g., 110) controlling multi-modal output of the machine (e.g., 120) in accordance with selected conversational content (process S810); a control system (e.g., 121) providing first event information to an evaluation system based on sensing of a human interaction participant by at least one sensor of the machine (e.g., a sensor of the multi-modal perceptual system 123) during processing of the selected conversational content by the conversation system (process S820); and the evaluation system providing evaluation results to an external client device (e.g., 190) based on the first event information (process S830).

Method 900

Figure 9:
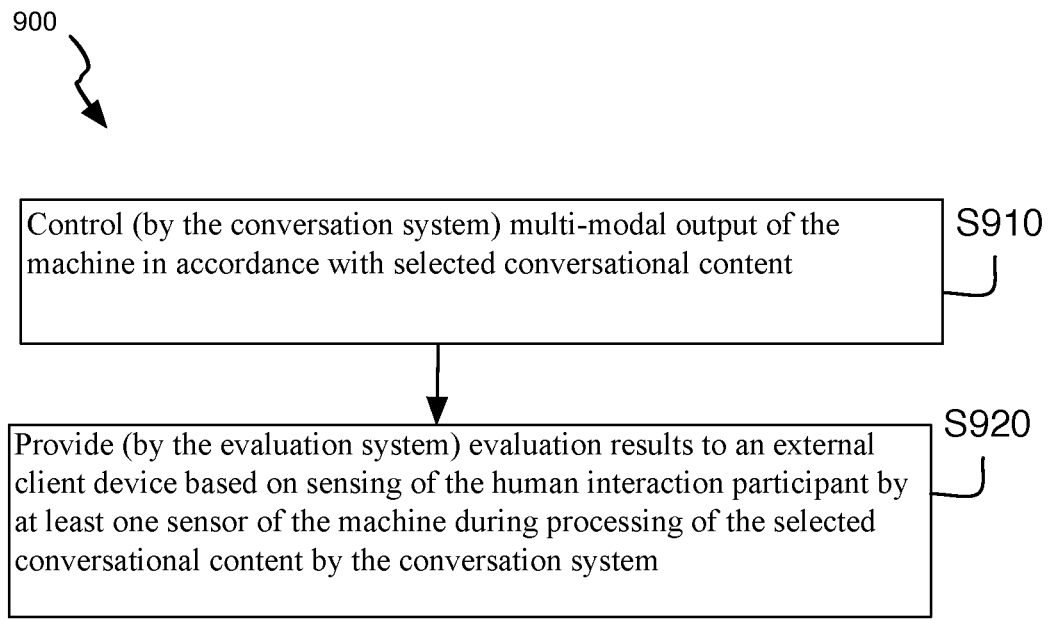

FIG. 9 is a representation of a method 900 according to embodiments. In some embodiments, at least one of the conversation system 110, the machine 120, the evaluation system 130, and the control system 121 performs the method 900. In some embodiments, at least one of the processes of the method 900 is similar to a process of the method 200.

In some embodiments, the method 900 includes: a conversation system (e.g., 110) controlling multi-modal output of the machine (e.g., 120) for a human interaction participant in accordance with selected conversational content (process S910); and an evaluation system providing evaluation results to an external client device (e.g., 190) based on sensing of the human interaction participant by at least one sensor of the machine during processing of the selected conversational content by the conversation system (process S920).

System Architecture

Figure 5:
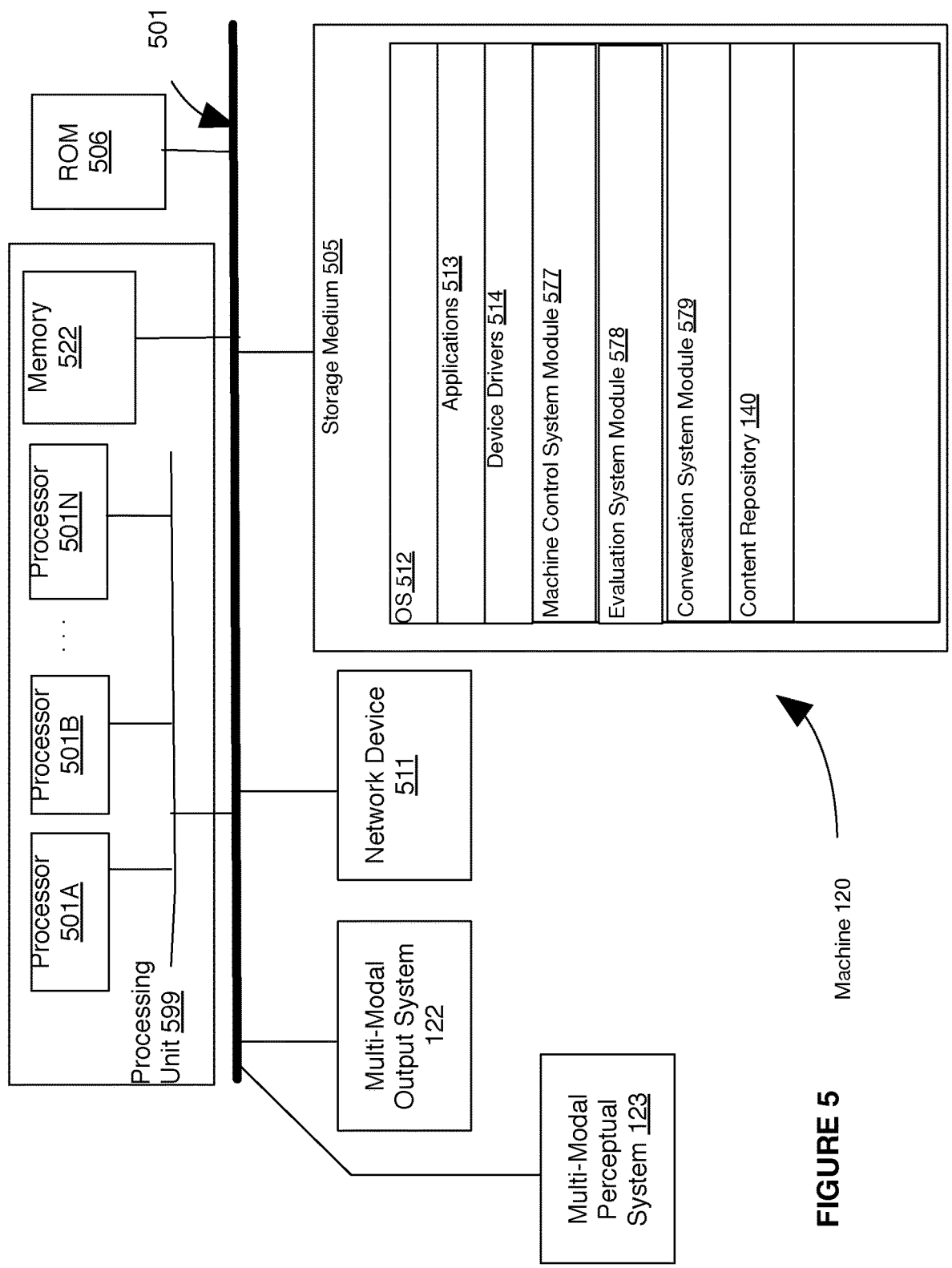
FIG. 5 is a diagram depicting system architecture of a system, according to embodiments.

FIG. 5 is a diagram depicting system architecture of machine (e.g., 120 of FIG. 1B-F), according to embodiments. In some embodiments, the system of FIG. 5 is implemented as a single hardware device. In some embodiments, the system of FIG. 5 is implemented as a plurality of hardware devices. In some embodiments, the system of FIG. 5 is implemented as an ASIC (Application-Specific Integrated Circuit). In some embodiments, the system of FIG. 5 is implemented as an FPGA (Field-Programmable Gate Array). In some embodiments, the system of FIG. 5 is implemented as a SoC (System-on-Chip). In some embodiments, the bus 501 interfaces with the processors 501A-N, the main memory 522 (e.g., a random access memory (RAM)), a read only memory (ROM) 506, a processor-readable storage medium 505, and a network device 511. In some embodiments, bus 501 interfaces with at least one of a display device (e.g., 102c) and a user input device.

In some embodiments, bus 501 interfaces with the multi-modal output system 122. In some embodiments, the multi-modal output system 122 includes an audio output controller. In some embodiments, the multi-modal output system 122 includes a speaker. In some embodiments, the multi-modal output system 122 includes a display system. In some embodiments, the multi-modal output system 122 includes a motor controller. In some embodiments, the motor controller is constructed to control an appendage (e.g., 105d) of the robot system of FIG. 1F. In some embodiments, the motor controller is constructed to control a motor of an appendage (e.g., 105d) of the robot system of FIG. 1F. In some embodiments, the motor controller is constructed to control a motor (e.g., a motor of a motorized, mechanical robot appendage).

In some embodiments, bus 501 interfaces with the multi-modal perceptual system 123. In some embodiments, the multi-modal perceptual system 123 includes an audio input processor. In some embodiments, the multi-modal perceptual system 123 includes a human reaction detection subsystem. In some embodiments, the multi-modal perceptual system 123 includes a microphone. In some embodiments, the multi-modal perceptual system 123 includes a camera.

In some embodiments, the processors include one or more of an ARM processor, an X86 processor, a GPU (Graphics Processing Unit), and the like. In some embodiments, at least one of the processors includes at least one arithmetic logic unit (ALU) that supports a SIMD (Single Instruction Multiple Data) system that provides native support for multiply and accumulate operations.

In some embodiments, at least one of a central processing unit (processor), a GPU, and a multi-processor unit (MPU) is included.

In some embodiments, the processors and the main memory form a processing unit 599. In some embodiments, the processing unit includes one or more processors communicatively coupled to one or more of a RAM, ROM, and machine-readable storage medium; the one or more processors of the processing unit receive instructions stored by the one or more of a RAM, ROM, and machine-readable storage medium via a bus; and the one or more processors execute the received instructions. In some embodiments, the processing unit is an ASIC (Application-Specific Integrated Circuit). In some embodiments, the processing unit is a SoC (System-on-Chip).

In some embodiments, the processing unit includes at least one arithmetic logic unit (ALU) that supports a SIMD (Single Instruction Multiple Data) system that provides native support for multiply and accumulate operations. In some embodiments the processing unit is a Central Processing Unit such as an Intel Xeon processor. In other embodiments, the processing unit includes a Graphical Processing Unit such as NVIDIA Tesla.

The network adapter device 511 provides one or more wired or wireless interfaces for exchanging data and commands. Such wired and wireless interfaces include, for example, a universal serial bus (USB) interface, Bluetooth interface, Wi-Fi interface, Ethernet interface, near field communication (NFC) interface, and the like.

In some embodiments, network device 511 is communicatively coupled to another machine (e.g., a machine similar to the machine 120 of FIGS. 1A-F In some embodiments, network device 511 is communicatively coupled to an evaluation system (e.g., 130). In some embodiments, network device 511 is communicatively coupled to a conversation system (e.g., 110). In some embodiments, network device 511 is communicatively coupled to a testing system (e.g., 150). In some embodiments, network device 511 is communicatively coupled to a content repository (e.g., 140). In some embodiments, network device 511 is communicatively coupled to a client device (e.g., 190). In some embodiments, network device 511 is communicatively coupled to a conversation authoring system (e.g., 160). In some embodiments, network device 511 is communicatively coupled to an evaluation module generator (e.g., 193). In some embodiments, network device 511 is communicatively coupled to a goal authoring system (e.g., 170). In some embodiments, network device 511 is communicatively coupled to a goal repository (e.g., 180).

Machine-executable instructions in software programs (such as an operating system, application programs, and device drivers) are loaded into the memory (of the processing unit) from the processor-readable storage medium, the ROM or any other storage location. During execution of these software programs, the respective machine-executable instructions are accessed by at least one of processors (of the processing unit) via the bus, and then executed by at least one of processors. Data used by the software programs are also stored in the memory, and such data is accessed by at least one of processors during execution of the machine-executable instructions of the software programs.

The processor-readable storage medium 505 is one of (or a combination of two or more of) a hard drive, a flash drive, a DVD, a CD, an optical disk, a floppy disk, a flash storage, a solid state drive, a ROM, an EEPROM, an electronic circuit, a semiconductor memory device, and the like. The processor-readable storage medium 505 includes machine-executable instructions (and related data) for an operating system 512, software programs 513, device drivers 514, and machine-executable instructions for one or more of the processes of FIG. 2.

In some embodiments, the processor-readable storage medium 505 includes a machine control system module 577 that includes machine-executable instructions for controlling the machine 120 to perform processes performed by the machine control system, as described herein.

In some embodiments, the processor-readable storage medium 505 includes an evaluation system module 578 that includes machine-executable instructions for controlling the machine 120 to perform processes performed by the evaluation system, as described herein.

In some embodiments, the processor-readable storage medium 505 includes a conversation system module 579 that includes machine-executable instructions for controlling the machine 120 to perform processes performed by the conversation system, as described herein.

In some embodiments, the processor-readable storage medium 505 includes machine-executable instructions for controlling the machine 120 to perform processes performed by the testing system, as described herein.

In some embodiments, the processor-readable storage medium 505 machine-executable instructions for controlling the machine 120 to perform processes performed by the conversation authoring system, as described herein.

In some embodiments, the processor-readable storage medium 505 machine-executable instructions for controlling the machine 120 to perform processes performed by the goal authoring system, as described herein.

In some embodiments, the processor-readable storage medium 505 includes machine-executable instructions for controlling the machine 120 to perform processes performed by the evaluation module generator, as described herein.

In some embodiments, the processor-readable storage medium 505 includes the content repository 140. In some embodiments, the processor-readable storage medium 505 includes the goal repository 180.

In some embodiments, the processor-readable storage medium 505 includes machine-executable instructions for an emotion detection module. In some embodiments, emotion detection module is constructed to detect an emotion based on captured image data (e.g., image data captured by the perceptual system 123). In some embodiments, emotion detection module is constructed to detect an emotion based on captured audio data (e.g., audio data captured by the perceptual system 123). In some embodiments, emotion detection module is constructed to detect an emotion based on captured image data and captured audio data. In some embodiments, emotions detectable by the emotion detection module include anger, contempt, disgust, fear, happiness, neutral, sadness, and surprise. In some embodiments, emotions detectable by the emotion detection module include happy, sad, angry, confused, disgusted, surprised, calm, unknown. In some embodiments, the emotion detection module is constructed to classify detected emotions as either positive, negative, or neutral. In some embodiments, the machine 120 uses the emotion detection module to obtain a determined emotion classification (e.g., positive, neutral, negative) after performance of an action by the machine, and store the determined emotion classification in association with the performed action (e.g., in the storage medium 505).

In some embodiments, the testing system 150 is a hardware device separate from the machine 120, and the testing system includes at least one processor, a memory, a ROM, a network device, and a storage medium (constructed in accordance with a system architecture similar to a system architecture described herein for the machine 120), wherein the storage medium stores machine-executable instructions for controlling the testing system 150 to perform processes performed by the testing system, as described herein.

In some embodiments, the conversation authoring system 160 is a hardware device separate from the machine 120, and the conversation authoring system 160 includes at least one processor, a memory, a ROM, a network device, and a storage medium (constructed in accordance with a system architecture similar to a system architecture described herein for the machine 120), wherein the storage medium stores machine-executable instructions for controlling the conversation authoring system 160 to perform processes performed by the conversation authoring system 160, as described herein.

In some embodiments, the evaluation module generator 193 is a hardware device separate from the machine 120, and the evaluation module generator 193 includes at least one processor, a memory, a ROM, a network device, and a storage medium (constructed in accordance with a system architecture similar to a system architecture described herein for the machine 120), wherein the storage medium stores machine-executable instructions for controlling the evaluation module generator 193 to perform processes performed by the evaluation module generator 193, as described herein.

In some embodiments, the goal authoring system 170 is a hardware device separate from the machine 120, and the goal authoring system 170 includes at least one processor, a memory, a ROM, a network device, and a storage medium (constructed in accordance with a system architecture similar to a system architecture described herein for the machine 120), wherein the storage medium stores machine-executable instructions for controlling the goal authoring system 170 to perform processes performed by the goal authoring system 170, as described herein. In some embodiments, the storage medium of the goal authoring system 170 includes data of the goal definition user interface described herein (e.g., the user interface of FIGS. 4A-C). In some embodiments, the storage medium of the goal authoring system 170 includes machine-executable instructions of the goal definition user interface described herein (e.g., the user interface of FIGS. 4A-C). In some embodiments, the storage medium of the goal authoring system 170 includes data of the goal definition information described herein (e.g., the goal definition information 301 of FIG. 3). In some embodiments, the storage medium of the goal authoring system 170 includes machine-executable instructions to control the goal authoring system to generate the goal definition information described herein (e.g., the goal definition information 301 of FIG. 3).

Machines

The systems and methods of some embodiments and variations thereof can be embodied and/or implemented at least in part as a machine configured to receive a computer-readable medium storing computer-readable instructions. The instructions are preferably executed by computer-executable components. The computer-readable medium can be stored on any suitable computer-readable media such as RAMs, ROMs, flash memory, EEPROMs, optical devices (CD or DVD), hard drives, floppy drives, or any suitable device. The computer-executable component is preferably a general or application specific processor, but any suitable dedicated hardware or hardware/firmware combination device can alternatively or additionally execute the instructions.

CONCLUSION

As a person skilled in the art will recognize from the previous detailed description and from the figures and claims, modifications and changes can be made to the embodiments disclosed herein without departing from the scope defined in the claims.

What is claimed is:

1. A method for controlling a machine comprising:
a conversation system controlling multi-modal output of the machine in accordance with selected conversational content;
a control system providing first event information to the conversation system based on sensing of a human interaction participant by at least one sensor of the machine during processing of the selected conversational content by the conversation system;
the conversation system controlling multi-modal output of the machine in accordance with the first event information;
an evaluation system updating conversational content used by the conversation system based on sensing of the human interaction participant by at least one sensor of the machine;
the evaluation system providing evaluation results to an external client device based on the sensing of the human interaction participant; and
a content authoring system generating the selected conversational content based on user-input received via a user input device;
further comprising: responsive to an instruction to evaluate a specified goal for the selected conversational content, the evaluation system enabling a goal evaluation module that is constructed to evaluate the specified goal, wherein the goal evaluation module controls the evaluation system to generate information indicating goal success for the specified goal based on a determination that a human interaction participant's response as sensed by a multi-modal perceptual system matches an expected response as defined by the generated selected conversational content.

2. The method of claim 1, further comprising: the conversation system performing a first conversation behavior associated with second event information received from the control system, in accordance with the selected conversational content.

3. The method of claim 1, further comprising: at least one of the control system or the evaluation system selecting the selected content based on at least one of:
sensing of the human interaction participant;
evaluation results;
content associated with successful evaluation results of similar human interaction participants;
history of previously used conversational content;
history of previously used conversational content and related evaluation results;
a specified conversational content schedule; or
a content selection instruction received from an external system.

4. The method of claim 1, wherein the evaluation system updates the conversational content based on at least one of:
sensing of the human interaction participant;
evaluation results;
content associated with successful evaluation results of similar human interaction participants;
history of previously used conversational content;
history of previously used conversational content and related evaluation results;
a specified interaction content schedule; or
a content selection instruction received from an external system.

5. The method of claim 1, wherein the selected conversational content specifies at least a first machine output and at least a first participant input associated with the first machine output, and at least one output of the selected conversational content is a conditional output that is associated with at least one of a goal, a goal level, or a participant support level.

6. The method of claim 5, wherein the goal is selectively enabled based on at least one of: sensing of the human interaction participant; evaluation results; content associated with successful evaluation results of similar human interaction participants; history of previously used conversational content; history of previously used conversational content and related evaluation results; a specified conversational content schedule; or an instruction received from an external system.

7. The method of claim 5, wherein the goal level is selectively enabled based on at least one of: sensing of the human interaction participant; evaluation results; content associated with successful evaluation results of similar human interaction participants; history of previously used conversational content; history of previously used conversational content and related evaluation results; a specified conversational content schedule; or an instruction received from an external system.

8. The method of claim 5, wherein the participant support level is selectively enabled based on at least one of: sensing of the human interaction participant; evaluation results; content associated with successful evaluation results of similar human interaction participants; history of previously used conversational content; history of previously used conversational content and related evaluation results; a specified conversational content schedule; or an instruction received from an external system.

9. The method of claim 1, wherein the selected conversational content relates to therapy and the evaluation results relate to an assessment of the human interaction participant's responsiveness to the therapy.

10. The method of claim 1, further comprising: a conversation testing system controlling a multi-modal output system of the machine, responsive to user-input received via a user input device of the conversation testing system; and the conversation testing system receiving event information from the machine indicating a human response sensed by the machine.

11. A method for controlling a machine comprising:
a conversation system controlling multi-modal output of the machine in accordance with selected conversational content;
a control system providing first event information to the conversation system based on sensing of a human interaction participant by at least one sensor of the machine during processing of the selected conversational content by the conversation system;
the conversation system controlling multi-modal output of the machine in accordance with the first event information;
an evaluation system updating conversational content used by the conversation system based on sensing of the human interaction participant by the at least one sensor of the machine;
the evaluation system providing evaluation results to an external client device based on the sensing of the human interaction participant; and
a content authoring system generating the selected conversational content based on user-input received via a user input device;
further comprising: responsive to an instruction to evaluate a specified goal for the selected conversational content, the evaluation system enabling a goal evaluation module that is constructed to evaluate the specified goal, wherein the goal evaluation module controls the evaluation system to generate information indicating goal success for the specified goal based on a determination that a human interaction participant's behavior as sensed by a multi-modal perceptual system matches an expected behavior.

12. The method of claim 11, wherein the evaluation system determines the expected behavior based on information received from at least one external system.

13. The method of claim 11, wherein the evaluation system determines the expected behavior based on information indicating behavior of similar human interaction participants during similar contexts.

14. The method of claim 11, wherein the evaluation system updates the conversational content based on supplemental information received from an external client device.

15. The method of claim 11, further comprising:
a conversation testing system controlling a multi-modal output system of the machine, responsive to user-input received via a user input device of the conversation testing system; and the conversation testing system receiving event information from the machine indicating a human response sensed by the machine.

16. A method for controlling a machine comprising:
a conversation system controlling multi-modal output of the machine in accordance with selected conversational content;
a control system providing first event information to the conversation system based on sensing of a human interaction participant by at least one sensor of the machine during processing of the selected conversational content by the conversation system;
the conversation system controlling multi-modal output of the machine in accordance with the first event information;
an evaluation system updating conversational content used by the conversation system based on sensing of the human interaction participant by at least one sensor of the machine;
the evaluation system providing evaluation results to an external client device based on the sensing of the human interaction participant; and
a goal authoring system providing a user interface to a client device, wherein the user interface includes at least one field for receiving user-input specifying at least a first goal, at least one field for receiving user-input specifying a goal evaluation module of the machine that is to be used to evaluate the first goal, at least one field for receiving user-input specifying at least a first goal level of the first goal, or at least one field for receiving user-input specifying at least a first participant support level of the first goal level.

17. The method of claim 16, further comprising: the goal authoring system automatically defining at least one goal level for the first goal.

18. The method of claim 16, further comprising: the goal authoring system automatically defining at least one participant support level for the first goal level.

19. The method of claim 16, further comprising: the goal authoring system determining available goal evaluation modules of the machine by communicating with the machine, and providing to the client device a user interface that identifies the determined available goal evaluation modules of the machine.

20. The method of claim 16, further comprising: a conversation testing system controlling a multi-modal output system of the machine, responsive to user-input received via a user input device of the conversation testing system; and the conversation testing system receiving event information from the machine indicating a human response sensed by the machine.

21. The method of claim 16, wherein the selected conversational content specifies at least a first machine output and at least a first human interaction participant input associated with the first machine output, and at least one output of the selected conversational content is a conditional output that is associated with at least one of a goal, a goal level, or a participant support level.

22. The method of claim 16, wherein the evaluation system updates the conversational content based on at least one of:
  sensing of the human interaction participant;
  evaluation results;
  content associated with successful evaluation results of similar human interaction participants;
  history of previously used conversational content;
  history of previously used conversational content and related evaluation results;
  a specified interaction content schedule; or
  a content selection instruction received from an external system.

23. The method of claim 16, wherein the selected conversational content specifies at least a first machine output and at least a first human interaction participant input associated with the first machine output, and at least one output of the selected conversational content is a conditional output that is associated with at least one of a goal, a goal level, or a participant support level.

\* \* \* \* \*